(12) United States Patent
Huang et al.

(10) Patent No.: US 10,870,936 B2
(45) Date of Patent: Dec. 22, 2020

(54) SOFT AND DURABLE NONWOVEN COMPOSITE

(71) Applicant: Kimberly-Clark Worldwide, Inc., Neenah, WI (US)

(72) Inventors: Lei Huang, Davidson, NC (US); Mark G. Kupelian, Atlanta, GA (US); Prasad Potnis, Johns Creek, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 79 days.

(21) Appl. No.: 15/028,953

(22) PCT Filed: Nov. 18, 2014

(86) PCT No.: PCT/IB2014/066133
§ 371 (c)(1),
(2) Date: Apr. 13, 2016

(87) PCT Pub. No.: WO2015/075631
PCT Pub. Date: May 28, 2015

(65) Prior Publication Data
US 2016/0251788 A1    Sep. 1, 2016

Related U.S. Application Data

(60) Provisional application No. 61/906,535, filed on Nov. 20, 2013.

(51) Int. Cl.
*D04H 1/4291* (2012.01)
*D04H 1/4374* (2012.01)
(Continued)

(52) U.S. Cl.
CPC .......... *D04H 1/4291* (2013.01); *A61F 13/00* (2013.01); *A61F 13/51* (2013.01);
(Continued)

(58) Field of Classification Search
CPC .............. A61F 13/00; A61F 13/00017; A61F 13/00029; A61F 13/00038–00046;
(Continued)

(56) References Cited

U.S. PATENT DOCUMENTS 3,338,992 A    8/1967    Kinney
3,341,394 A    9/1967    Kinney
(Continued)

FOREIGN PATENT DOCUMENTS

EP    2 479 331 A1    7/2012
EP    2010703    1/2013
(Continued)

OTHER PUBLICATIONS

Wiley-VCH. (2016). Ullmann's Polymers and Plastics—Products and Processes, 4 Volume Set—24.2.2 Polyethylene: General Properties. John Wiley & Sons. Retrieved from https://app.knovel.com/hotlink/pdf/id:kt011CARV1/ullmanns-polymers-plastics/unimodal-multimodal-polyethylene (Year: 2016).*
(Continued)

*Primary Examiner* — Laura C Powers
*Assistant Examiner* — Larissa Rowe Emrich
(74) *Attorney, Agent, or Firm* — Dority & Manning, P.A.

(57) ABSTRACT

A nonwoven composite that contains a first nonwoven web positioned adjacent to a second nonwoven web is provided. The first nonwoven web contains a plurality of fibers that are formed from a first polyolefin composition, and the second nonwoven web contains a plurality of fibers that are formed from a second polyolefin composition. The first polyolefin composition contains an ethylene polymer, which and car; provide a soft feel to a surface of the first nonwoven web. The second polyolefin composition likewise contains a rigid propylene polymer, which can provide good strength and durability to the second nonwoven web. The second poly-
(Continued)

olefin composition also contains a ductile propylene polymer and a fatty acid derivative.

24 Claims, 1 Drawing Sheet

(51) Int. Cl.

| | | |
|---|---|---|
| *D04H 3/007* | (2012.01) | |
| *B32B 5/08* | (2006.01) | |
| *B32B 5/02* | (2006.01) | |
| *B32B 5/26* | (2006.01) | |
| *A61F 13/51* | (2006.01) | |
| *A61F 13/514* | (2006.01) | |
| *B32B 27/12* | (2006.01) | |
| *B32B 27/32* | (2006.01) | |
| *B32B 27/34* | (2006.01) | |
| *B32B 27/30* | (2006.01) | |
| *B32B 7/12* | (2006.01) | |
| *B32B 27/36* | (2006.01) | |
| *B32B 7/05* | (2019.01) | |
| *A61F 13/00* | (2006.01) | |

(52) U.S. Cl.
CPC .... *A61F 13/5148* (2013.01); *A61F 13/51478* (2013.01); *B32B 5/022* (2013.01); *B32B 5/08* (2013.01); *B32B 5/26* (2013.01); *B32B 7/05* (2019.01); *B32B 7/12* (2013.01); *B32B 27/12* (2013.01); *B32B 27/302* (2013.01); *B32B 27/304* (2013.01); *B32B 27/32* (2013.01); *B32B 27/322* (2013.01); *B32B 27/327* (2013.01); *B32B 27/34* (2013.01); *B32B 27/36* (2013.01); *D04H 1/4374* (2013.01); *D04H 3/007* (2013.01); *A61F 2013/51026* (2013.01); *B32B 2250/02* (2013.01); *B32B 2250/03* (2013.01); *B32B 2250/20* (2013.01); *B32B 2250/40* (2013.01); *B32B 2262/0253* (2013.01); *B32B 2307/50* (2013.01); *B32B 2307/546* (2013.01); *B32B 2307/554* (2013.01); *B32B 2307/718* (2013.01); *B32B 2439/46* (2013.01); *B32B 2535/00* (2013.01); *B32B 2555/00* (2013.01); *B32B 2555/02* (2013.01)

(58) Field of Classification Search
CPC ................ A61F 13/51; A61F 13/51478; A61F 13/5148; A61F 2013/51023–51026; A61F 2013/15121–1513; A61F 2013/51002; A61F 2013/51165–51182; A61F 2103/51409; A61F 2013/51441; A61F 2013/51452; A61F 13/51121; A61F 13/5116; A61F 13/51401; A61F 13/51464–51466; B32B 7/00; B32B 7/02; B32B 27/12; B32B 27/32; B32B 27/327; B32B 2250/00–20; B32B 2250/24–242; B32B 2262/0253; B32B 2305/10–20; B32B 2323/10; B32B 2555/02; B32B 5/02–022; B32B 5/22–24; B32B 5/26; B32B 27/00–02; B32B 2250/02–20; B32B 2262/00–0215; B32B 2262/14; B32B 2270/00; B32B 2307/51; B32B 2307/546; B32B 2307/582–5825; B32B 2307/726; B32B 2432/00; B32B 2555/00–02; D04H 1/4291; D04H 1/4374; D04H 3/007; D04H 3/005; D10B 2321/021; D10B 2321/022; D10B 2509/026

USPC ........ 442/328–329, 333, 381–384, 387–392, 442/397–398, 400–411, 415–416
See application file for complete search history.

(56) References Cited

U.S. PATENT DOCUMENTS

| | | | |
|---|---|---|---|
| 3,454,519 A | | 7/1969 | Hulse et al. |
| 3,485,706 A | | 12/1969 | Evans |
| 3,502,538 A | | 3/1970 | Petersen |
| 3,502,763 A | | 3/1970 | Hartmann |
| 3,542,615 A | | 11/1970 | Dobo et al. |
| 3,692,618 A | | 9/1972 | Dorschner et al. |
| 3,802,817 A | | 4/1974 | Matsuki et al. |
| 3,849,241 A | | 11/1974 | Butin et al. |
| 3,855,046 A | | 12/1974 | Hansen et al. |
| 4,041,203 A | | 8/1977 | Brock et al. |
| 4,215,682 A | | 8/1980 | Kubik et al. |
| 4,340,563 A | | 7/1982 | Appel et al. |
| 4,374,888 A | | 2/1983 | Bornslaeger |
| 4,375,718 A | | 3/1983 | Wadsworth et al. |
| 4,592,815 A | | 6/1986 | Nakao |
| 4,644,045 A | * | 2/1987 | Fowells ............... C08F 210/16 264/210.8 |
| 4,704,116 A | | 11/1987 | Enloe |
| 4,766,029 A | | 8/1988 | Brock et al. |
| 4,778,460 A | * | 10/1988 | Braun ............... A61F 13/15658 428/172 |
| 4,789,592 A | | 12/1988 | Taniguchi et al. |
| 4,795,668 A | | 1/1989 | Krueger et al. |
| 4,874,659 A | | 10/1989 | Ando et al. |
| 4,965,122 A | | 10/1990 | Morman |
| 4,981,747 A | | 1/1991 | Morman |
| 5,023,130 A | | 6/1991 | Simpson et al. |
| 5,057,368 A | | 10/1991 | Largman et al. |
| 5,069,970 A | | 12/1991 | Largman et al. |
| 5,108,820 A | | 4/1992 | Kaneko et al. |
| 5,162,074 A | | 11/1992 | Hills |
| 5,169,706 A | | 12/1992 | Collier, IV et al. |
| 5,192,606 A | | 3/1993 | Proxmire et al. |
| 5,213,881 A | | 5/1993 | Timmons et al. |
| 5,226,992 A | | 7/1993 | Morman |
| 5,272,236 A | | 12/1993 | Lai et al. |
| 5,277,976 A | | 1/1994 | Hogle et al. |
| 5,322,728 A | | 6/1994 | Davey et al. |
| 5,336,545 A | | 8/1994 | Morman |
| 5,336,552 A | | 8/1994 | Strack et al. |
| 5,382,400 A | | 1/1995 | Pike et al. |
| 5,401,446 A | | 3/1995 | Tsai et al. |
| 5,460,884 A | | 10/1995 | Kobylivker et al. |
| 5,464,688 A | | 11/1995 | Timmons et al. |
| 5,466,410 A | | 11/1995 | Hills |
| 5,472,775 A | | 12/1995 | Obijeski et al. |
| 5,486,166 A | | 1/1996 | Bishop et al. |
| 5,490,846 A | | 2/1996 | Ellis et al. |
| 5,539,056 A | * | 7/1996 | Yang ..................... C08L 23/10 525/240 |
| 5,571,619 A | * | 11/1996 | McAlpin ............... C08F 210/06 428/364 |
| 5,596,052 A | | 1/1997 | Resconi et al. |
| 5,620,779 A | | 4/1997 | Levy et al. |
| 5,626,571 A | | 5/1997 | Young et al. |
| 5,652,194 A | | 7/1997 | Dyer et al. |
| 5,695,868 A | | 12/1997 | McCormack |
| 5,702,377 A | | 12/1997 | Collier, IV et al. |
| D390,708 S | | 2/1998 | Brown |
| 5,723,546 A | | 3/1998 | Sustic |
| 5,766,737 A | | 6/1998 | Willey et al. |
| 5,806,155 A | | 9/1998 | Malaney et al. |
| 5,843,057 A | | 12/1998 | McCormack |
| 5,855,999 A | | 1/1999 | McCormack |
| 5,883,026 A | | 3/1999 | Reader et al. |
| 5,908,598 A | | 6/1999 | Rousseau et al. |
| 5,931,823 A | | 8/1999 | Stokes et al. |
| 5,932,497 A | | 8/1999 | Morman et al. |
| 5,962,112 A | | 10/1999 | Haynes et al. |
| 5,997,981 A | | 12/1999 | McCormack et al. |

(56) References Cited

U.S. PATENT DOCUMENTS

| | | | |
|---|---|---|---|
| 6,002,064 A | 12/1999 | Kobylivker et al. |
| 6,015,764 A | 1/2000 | McCormack et al. |
| 6,037,281 A | 3/2000 | Mathis et al. |
| 6,060,638 A | 5/2000 | Paul et al. |
| D428,267 S | 7/2000 | Romano, III et al. |
| 6,090,325 A | 7/2000 | Wheat et al. |
| 6,090,730 A | 7/2000 | Fujiwara et al. |
| 6,093,665 A | 7/2000 | Sayovitz et al. |
| 6,110,848 A | 8/2000 | Bouchette |
| 6,111,163 A | 8/2000 | McCormack et al. |
| 6,150,002 A | 11/2000 | Varona |
| 6,200,669 B1 | 3/2001 | Marmon et al. |
| 6,228,462 B1 | 5/2001 | Lee et al. |
| 6,321,425 B1 | 11/2001 | Putnam et al. |
| 6,365,088 B1 | 4/2002 | Knight et al. |
| 6,430,788 B1 | 8/2002 | Putnam et al. |
| 6,448,194 B2 | 9/2002 | Gessner et al. |
| 6,461,457 B1 | 10/2002 | Taylor et al. |
| 6,500,563 B1 | 12/2002 | Datta et al. |
| 6,632,385 B2 | 10/2003 | Kauschke et al. |
| 6,657,033 B1 | 12/2003 | Sartori et al. |
| 6,663,611 B2 | 12/2003 | Blaney et al. |
| 6,715,189 B2 | 4/2004 | Osbon et al. |
| 6,740,609 B1 | 5/2004 | Peng et al. |
| 6,782,589 B2 | 8/2004 | Ngai |
| 6,797,377 B1 | 9/2004 | DeLucia et al. |
| 6,852,654 B2 | 2/2005 | Fuller et al. |
| 6,903,034 B1 | 6/2005 | Putnam et al. |
| 7,060,867 B2 | 6/2006 | Jameson |
| 7,091,140 B1 | 8/2006 | Ferencz et al. |
| 7,319,122 B2 | 1/2008 | Cheng et al. |
| 7,320,948 B2 | 1/2008 | Morman et al. |
| 7,367,093 B2 | 5/2008 | Fleissner |
| 7,406,755 B2 | 8/2008 | Putnam et al. |
| 7,455,800 B2 | 11/2008 | Ferencz et al. |
| 7,803,146 B2 | 9/2010 | Wada et al. |
| 7,858,544 B2 | 12/2010 | Turi et al. |
| 7,902,093 B2 | 3/2011 | Dharmarajan et al. |
| 8,093,163 B2 | 1/2012 | Turi et al. |
| 8,410,007 B2 | 4/2013 | Turi et al. |
| 8,470,915 B2 | 6/2013 | Li et al. |
| 8,510,922 B2 | 8/2013 | Turi et al. |
| 8,647,741 B2 | 2/2014 | Katayama et al. |
| 8,709,191 B2 | 4/2014 | Hughes et al. |
| 8,722,963 B2 | 5/2014 | Kanya et al. |
| 8,841,507 B2 | 9/2014 | Kanya et al. |
| 8,974,431 B2 | 3/2015 | Lawson et al. |
| 8,980,964 B2 | 3/2015 | Topolkaraev et al. |
| 9,050,777 B2 | 6/2015 | Kauschke et al. |
| 9,260,808 B2 | 2/2016 | Schmidt et al. |
| 2001/0005662 A1* | 6/2001 | Gessner ................. B32B 5/04 |
| | | 442/290 |
| 2001/0037850 A1 | 11/2001 | Marmon et al. |
| 2003/0157859 A1 | 8/2003 | Ishikawa |
| 2004/0005457 A1 | 1/2004 | DeLucia et al. |
| 2004/0110442 A1 | 6/2004 | Rhim et al. |
| 2005/0054255 A1 | 3/2005 | Morman et al. |
| 2005/0059941 A1 | 3/2005 | Baldwin et al. |
| 2005/0106978 A1 | 5/2005 | Cheng et al. |
| 2005/0230034 A1 | 10/2005 | Arora et al. |
| 2006/0151914 A1 | 7/2006 | Gerndt et al. |
| 2006/0183860 A1* | 8/2006 | Mehta ................... C08L 23/10 |
| | | 525/191 |
| 2007/0028348 A1 | 2/2007 | Turney |
| 2007/0173162 A1 | 7/2007 | Ethiopia et al. |
| 2009/0053959 A1 | 2/2009 | Datta et al. |
| 2009/0054861 A1 | 2/2009 | Watson et al. |
| 2009/0061185 A1 | 3/2009 | Hisamoto |
| 2009/0111347 A1* | 4/2009 | Peng .................... D01F 1/10 |
| | | 442/334 |
| 2009/0118689 A1 | 5/2009 | Lawson et al. |
| 2010/0168704 A1 | 7/2010 | Thomas et al. |
| 2011/0009843 A1 | 1/2011 | Krook |
| 2012/0179125 A1 | 7/2012 | Kanya et al. |
| 2012/0189814 A1 | 7/2012 | Coslett et al. |
| 2012/0208422 A1 | 8/2012 | Koori et al. |
| 2012/0219776 A1 | 8/2012 | Vignola et al. |
| 2012/0302982 A1 | 11/2012 | Takebe et al. |
| 2013/0237938 A1 | 9/2013 | Autran et al. |
| 2013/0309931 A1* | 11/2013 | Koori ................... D04H 3/147 |
| | | 442/401 |
| 2015/0368836 A1 | 12/2015 | Koori et al. |
| 2016/0251788 A1 | 9/2016 | Huang et al. |

FOREIGN PATENT DOCUMENTS

| | | | |
|---|---|---|---|
| WO | WO 96/06966 | 3/1996 | |
| WO | WO 00/39201 | 7/2000 | |
| WO | WO-2012105567 A1 * | 8/2012 | ............. D04H 3/147 |
| WO | WO 2012/134988 | 10/2012 | |
| WO | WO 2014/074409 A1 | 5/2014 | |
| WO | WO 2015/075632 A1 | 5/2015 | |
| WO | WO 2016/080960 A1 | 5/2016 | |

OTHER PUBLICATIONS

Annex to the European Patent Application No. EP 14 86 3365 dated Jul. 7, 2017, 6 pages.

International Preliminary Report on Patentability dated Sep. 9, 2016, 8 pages.

Abstract of Korean Patent—KR1004582310000, Apr. 6, 2005, 2 pages.

Abstract of Japanese Patent—JPH08134762, May 28, 1996, 1 page.

Abstract of Japanese Patent—JPH08176923, Jul. 9, 1996, 1 page.

Abstract of Japanese Patent—JPH08199423, Aug. 6, 1996, 1 page.

Idemitsu Kosan Co., Ltd., Soft Nonwoven Fabrics and L-MODU™ S901 & S600, PowerPoint Presentation, 10 pages.

ExxonMobil Chemical, Improve elasticity, processing efficiency of nonwoven consumer and industrial products, http://www.exxonmobilchemical.com/Chem-English/yourindustry/nonwoven-consumer-industrial.asps, 1 page.

ExxonMobil Chemical, ExxonMobil™ PP3155 Polypropylene Homopolymer, (product information) 2 pages.

Idemitsu Kosan Co., Ltd., Chemicals Development Center, Performance Chemicals Department, The Performance of L-MODU™ for HMA Base Polymer Use, Aug. 2011, 15 pages.

ExxonMobil PP3155 Homopolymer Grade for Nonwoven and Fiber Applications, http://matweb.com/search/Datasheet.aspx?MatGUID=d32d7bd5fled4cldbd86e2b7f6b63297, (product information) 2 pages.

Mukul Kaushik, New Low Density and Low Hardness Thermoplastic Co-polyester Elastomers (COPE), 5 pages.

L-MODU (Low Molecular weight and Low Modulus polypropylene), http://www.idemitsu.com/products/petrochemicals/chemicals/Impo.html, 3 pages.

XZ 89203.03 Experimental Polythylene Resin, DOW, (product information) 3 pages.

International Search Report and Written Opinion for PCT/IB2014/066134, dated Feb. 26, 2015, 10 pages.

* cited by examiner

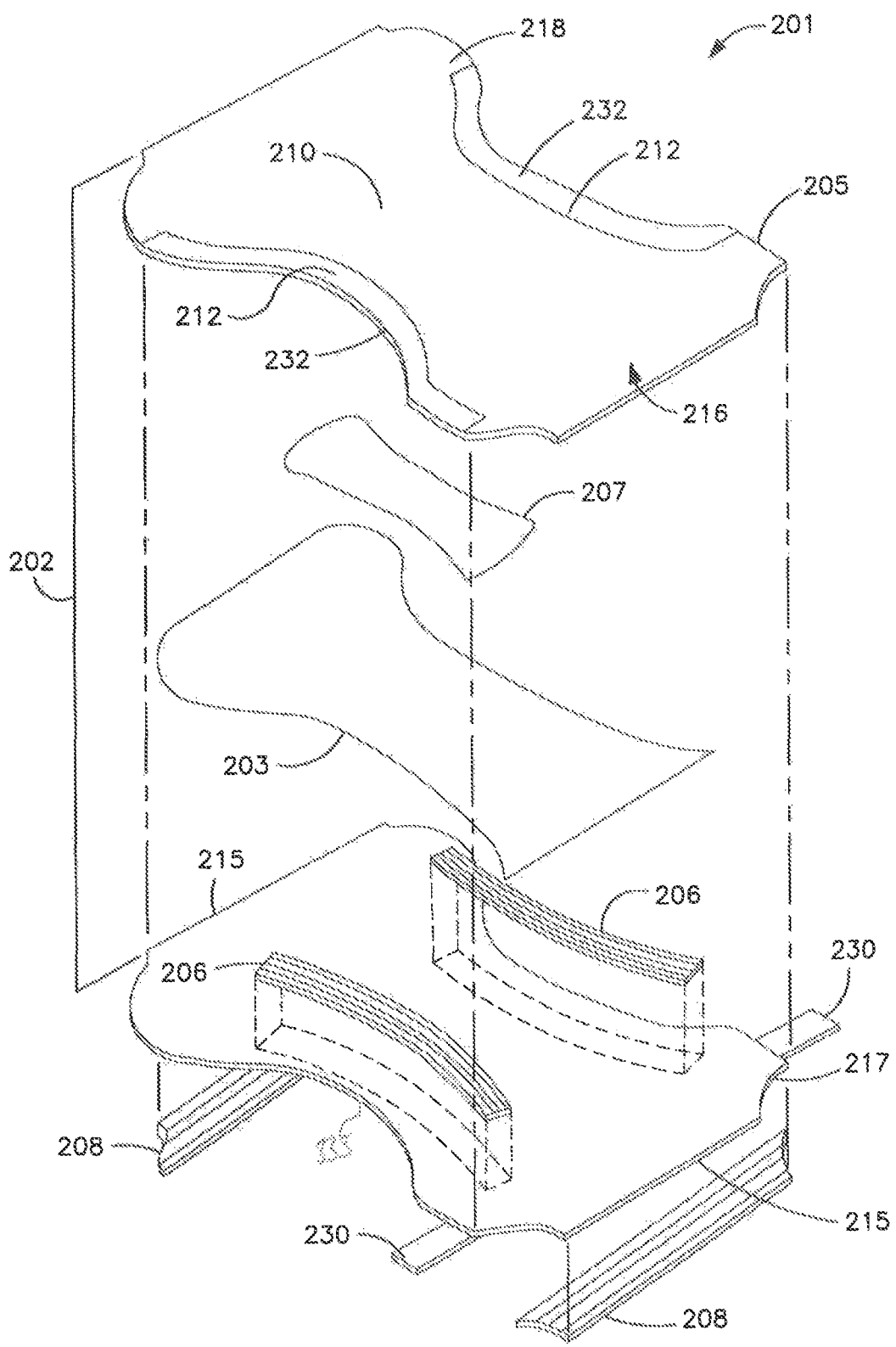

SOFT AND DURABLE NONWOVEN COMPOSITE

RELATED APPLICATIONS

The present application is the national stage entry of International Patent Application No. PCT/IB2014/066133 having a filing date of Nov. 18, 2014, which claims priority to U.S. Provisional Application Ser. No. 61/906,535, filed on Nov. 20, 2013, which are incorporated herein in their entirety by reference thereto.

BACKGROUND OF THE INVENTION

Nonwoven webs or fabrics are desirable for use in a variety of products such as disposable diapers and other personal hygiene products. For example, in a disposable diaper, it is highly desirable to have nonwoven components that are both soft and strong. Backsheets, for instance, are often formed from a polypropylene nonwoven web laminated to a breathable film made from linear low density polyethylene. One of the problems with conventional backsheets, however, is that they generally lack a soft, cloth-like feel. The polypropylene nonwoven web, for instance, can be relative rigid in nature and have a rough feel on its surface. For these reasons, various attempts have been made to improve the softness of the nonwoven web through mechanical post treatments. For example, one technique that has been attempted involves reducing the degree of thermal bonding (e.g., decreasing the size or distance between bond sites) in the nonwoven web. Unfortunately, however, this can lead to an increased degree of abrasion (e.g., fuzzing or lint). Because abrasion resistance correlates to fuzzing, known methods of nonwoven web production generally result in a tradeoff between the fuzzing and softness properties of the nonwoven web.

As such, a need currently exists for a nonwoven web material that can exhibit a soft and cloth-like feel without a substantial reduction in durability (e.g., abrasion resistance) or strength.

SUMMARY OF THE INVENTION

In accordance with one embodiment of the present invention, a nonwoven composite is disclosed that comprises a first nonwoven web containing a plurality of fibers formed from a first polyolefin composition and a second nonwoven web positioned adjacent to the first nonwoven web and containing a plurality of fibers formed from a second polyolefin composition. The first polyolefin composition contains at least one ethylene polymer, and the second polyolefin composition contains at least one rigid propylene polymer, at least one ductile propylene polymer, and at least one fatty acid derivative.

Other features and aspects of the present invention are described in more detail below.

BRIEF DESCRIPTION OF THE DRAWING

A full and enabling disclosure of the present invention, including the best mode thereof, directed to one of ordinary skill in the art, is set forth more particularly in the remainder of the specification, which makes reference to the appended FIGURE in which:

FIG. 1 is a perspective view of an absorbent article that may be formed in accordance with one embodiment of the present invention.

Repeat use of reference characters in the present specification and drawing is intended to represent same or analogous features or elements of the invention.

DETAILED DESCRIPTION OF REPRESENTATIVE EMBODIMENTS

Definitions

As used herein, the term "fibers" generally refer to elongated extrudates that may be formed by passing a polymer through a forming orifice, such as a die. Unless noted otherwise, the term "fibers" includes discontinuous fibers having a definite length (e.g., stable fibers) and substantially continuous filaments. Substantially filaments may, for instance, have a length much greater than their diameter, such as a length to diameter ratio ("aspect ratio") greater than about 15,000 to 1, and in some cases, greater than about 50,000 to 1.

As used herein the term "nonwoven web" generally refers to a web having a structure of fibers that are interlaid, but not in an identifiable manner as in a knitted fabric. Examples of suitable nonwoven webs include, but are not limited to, meltblown webs, spunbond webs, bonded carded webs, airlaid webs, coform webs, hydraulically entangled webs, and so forth.

As used herein, the term "spunbond" web generally refers to a nonwoven web containing substantially continuous filaments formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al.

As used herein, the term "meltblown" web or facing generally refers to a nonwoven web containing fibers formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a nonwoven composite that contains a first nonwoven web positioned adjacent to a second nonwoven web. The first nonwoven web contains a plurality of fibers that are formed from a first polyolefin composition, and the second nonwoven web contains a plurality of fibers that are formed from a second polyolefin composition. The first polyolefin composition contains an ethylene polymer having a relatively low melting temperature and modulus of elasticity, which and can provide a soft feel to a surface of the first nonwoven web. The second polyolefin composition likewise contains a rigid propylene polymer that has a relatively high melting temperature and modulus of elasticity, which can provide good strength and durability to the second nonwoven web. Due to the vastly different melting temperatures of the ethylene polymer and rigid propylene polymer, it is relatively difficult to achieve good bonding between the different nonwoven web layers of the composite. Furthermore, the rigid propylene polymer has a relatively stiff feel, which is not ideal. Nevertheless, despite containing such a rigid, high melting point polymer, the present inventors have surprisingly discovered that, through the use of certain components in the second polyolefin composition, the second nonwoven web can not only achieve good bonding to the first nonwoven web, but it can also have a soft and ductile feel.

More particularly, the second polyolefin composition contains a ductile propylene polymer and a fatty acid derivative in combination with the rigid propylene polymer. Among other things, the ductile propylene polymer can reduce stiffness and also broaden the window of temperatures at which the second polyolefin composition begins to melt, thereby making it easier to bond the compositions together at a temperature that more closely approximates that of the first polyolefin composition. Likewise, the fatty acid derivative can significantly improve the softness of the composition. By selectively controlling the weight ratio of each of these components within a certain range, the present inventors have discovered that the softness, ductility, and adhesive properties of the composition can all be dramatically improved without having a significant adverse impact on the durability and strength of the resulting web. For example, the weight ratio of ductile polymers to fatty acid derivatives typically ranges from about 2 to about 60, in some embodiments from about 10 to about 50, in some embodiments from about 15 to about 40, and in some embodiments, from about 20 to about 30.

In this regard, various embodiments of the present invention will now be described in more detail.

I. First Polyolefin Composition

As indicated above, the first polyolefin composition contains an ethylene polymer. Ethylene polymers generally constitute about 80 wt. % or more, in some embodiments about 90 wt. % or more, and in some embodiments, from about 92 wt. % to 100 wt. % of the polymer content of the first polyolefin composition. Of course, the actual amount of such polymers may vary depending on the presence of any optional additives in the composition. Examples of such additives may include, for instance, fillers, pigments, antioxidants, stabilizers (e.g., melt stabilizers, light stabilizers, heat stabilizers, etc.), surfactants, flow promoters, solid solvents, plasticizers, particulates, bonding agents, tackifiers, viscosity modifiers, etc. When employed, additives typically constitute from about 0.001 wt. % to about 10 wt. %, in some embodiments from about 0.01 wt. % to about 8 wt. %, and in some embodiments, from about 0.1 wt. % to about 5 wt. % of the first polyolefin composition. Likewise, ethylene polymers may constitute from about 90 wt. % to about 99.999 wt. %, in some embodiments from about 92 wt. % to about 99.99 wt. %, and in some embodiments, from about 95 wt. % to about 99.9 wt. % of the first polyolefin composition.

As noted above, the ethylene polymer employed typically has a relatively low melting temperature and modulus of elasticity, which can provide the resulting nonwoven web with a relatively soft and ductile feel. For example, the ethylene polymer may have a melting temperature of from about 50° C. to about 145° C., in some embodiments from about 75° C. to about 140° C., and in some embodiments, from about 100° C. to about 135° C., and a modulus of elasticity of from about 50 to about 700 MPa, in some embodiments from about 75 to about 600 MPa, and in some embodiments, from about 100 to about 500 MPa, as determined in accordance with ASTM D638-10. The melting temperature of the entire first polyolefin composition may likewise range from about 50° C. to about 145° C., in some embodiments from about 75° C. to about 140° C., and in some embodiments, from about 100° C. to about 135° C. The modulus of elasticity of the composition may also range from about 50 to about 700 MPa, in some embodiments from about 75 to about 600 MPa, and in some embodiments, from about 100 to about 500 MPa, as determined in accordance with ASTM D638-10. The ethylene polymer may also have a melt flow index of from about 1 to about 100 grams per 10 minutes, in some embodiments from about 5 to about 50 grams per 10 minutes, and in some embodiments, from about 10 to about 40 grams per 10 minutes, determined at a load of 2160 grams and at 190° C., as determined in accordance with ASTM 01238-13 (or ISO 1133).

Any of a variety of ethylene polymers may generally be employed in the present invention. In one embodiment, for instance, the ethylene polymer may be a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %. The density of the polyethylene may vary depending on the type of polymer employed, but generally ranges from about 0.85 to about 0.96 grams per cubic centimeter ($g/cm^3$). Polyethylene "plastomers", for instance, may have a density in the range of from about 0.85 to about 0.91 $g/cm^3$. Likewise, "linear low density polyethylene" (LLDPE) may have a density in the range of from about 0.91 to about 0.940 $g/cm^3$; "low density polyethylene" (LDPE) may have a density in the range of from about 0.910 to about 0.940 $g/cm^3$; and "high density polyethylene" (HDPE) may have density in the range of from about 0.940 to about 0.960 $g/cm^3$, such as determined in accordance with ASTM 1505-10. LLDPE may be particularly suitable for use in the first polyolefin composition.

Any of a variety of known techniques may generally be employed to form the ethylene polymer. For instance, olefin polymers may be formed using a free radical or a coordination catalyst (e.g., Ziegler-Natta). Typically, the ethylene polymer is formed from a single-site coordination catalyst, such as a metallocene catalyst. Such a catalyst system produces ethylene polymers in which a comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

II. Second Polyolefin Composition

A. Rigid Propylene Polymer

While soft, the first polyolefin composition does not typically provide sufficient durability and mechanical strength to the composite for use in various applications. In this regard, the second polyolefin composition may contain a rigid propylene polymer, which has a relatively high melting temperature and modulus of elasticity. For example, the rigid propylene polymer may have a melting temperature of from about 145° C. to about 200° C., in some embodiments from about 150° C. to about 180° C., and in some embodiments, from about 155° C. to about 170° C., and a modulus of elasticity of from about 800 to about 4,000 MPa, in some embodiments from about 1,000 to about 3,000 MPa, and in some embodiments, from about 1,200 to about 2,500 MPa, as determined in accordance with ASTM D638-10. The rigid propylene polymer may also have a melt flow index of from about 15 to about 100 grams per 10 minutes, in some embodiments from about 20 to about 80 grams per 10 minutes, and in some embodiments, from about 25 to about 50 grams per 10 minutes, determined at a load of 2160 grams and at 230° C., as determined in accordance with ASTM D1238-13 (or ISO 1133).

Any of a variety of propylene polymers having the characteristics noted above may generally be employed in the present invention. In one particular embodiment, for instance, the propylene polymer is an isotactic or syndiotactic homopolymer or copolymer (e.g., random or block) containing about 10 wt. % or less of co-monomers (e.g., α-olefins), and in some embodiments, about 2 wt. % or less. The term "syndiotactic" generally refers to a tacticity in which a substantial portion, if not all, of the methyl groups alternate on opposite sides along the polymer chain. On the other hand, the term "isotactic" generally refers to a tacticity in which a substantial portion, if not all, of the methyl groups are on the same side along the polymer chain. Such polymers are typically formed using a Ziegler-Natta catalyst, either alone or in combination with a small amount of an α-olefin co-monomer. Isotactic polymers, for instance, typically have a density in the range of from 0.88 to 0.94 g/cm³, and in some embodiments, from about 0.89 to 0.91 g/cm³, such as determined in accordance with ASTM 1505-10. Commercially available rigid propylene homopolymers may include, for instance, Metocene™ MF650Y and MF650X, which are available from Basel Polyolefins, as well as PP 3155, which is available from Exxon Mobil. Other examples of suitable propylene polymers may be described in U.S. Pat. No. 6,500,563 to Datta, et al; U.S. Pat. No. 5,539,056 to Yana, et al.; and U.S. Pat. No. 5,596,052 to Resconi, et al.

Rigid propylene polymers generally constitute from about 80 wt. % to about 99.5 wt. %, in some embodiments from about 85 wt. % to about 99 wt. %, and in some embodiments, from about 90 wt. % to 98 wt. % of the polymer content of the second polyolefin composition. Likewise, the rigid propylene polymers may constitute from about 80 wt. % to about 99.5 wt. %, in some embodiments from about 85 wt. % to about 99 wt. %, and in some embodiments, from about 90 wt. % to 98 wt. % of the entire second polyolefin composition.

B. Ductile Propylene Polymer

The ductile propylene polymer may have a relatively low modulus of elasticity in comparison with the rigid propylene polymer, which further reduces the overall stiffness of the second polyolefin composition. For example, the ratio of the modulus of elasticity of the rigid propylene polymer to that of the ductile propylene polymer is typically from about 1 to about 50, in some embodiments from about 2 to about 40, and in some embodiments, from about 5 to about 30. The modulus of elasticity of the ductile propylene polymer may, for instance, range from about 1 to about 500 MPa, in some embodiments from about 5 to about 300 MPa, and in some embodiments, from about 10 to about 100 MPa, as determined in accordance with ASTM D638-10. The ductile propylene polymer may also have a relatively low melt flow index, such as from about 15 to about 1,000 grams per 10 minutes, in some embodiments from about 20 to about 500 grams per 10 minutes, and in some embodiments, from about 25 to about 200 grams per 10 minutes, determined at a load of 2160 grams and at 230° C., as determined in accordance with ASTM D1238-13 (or ISO 1133). Of course, in other embodiments, polymers with a relatively high melt flow index may be employed, such as from about 1,000 to about 5,000 grams per 10 minutes, in some embodiments from about 1,500 to about 4,000 grams per 10 minutes, and in some embodiments, from about 1,600 to about 3,000 grams per 10 minutes, determined at a load of 2160 grams and at 230° C., as determined in accordance with ASTM D1238-13 (or ISO 1133).

In addition, the ductile propylene polymer may also have a relatively low melting point and a relatively low degree of crystallinity. For example, the melting temperature of the ductile polymer may be from about 40° C. to about 120° C., in some embodiments from about 50° C. to about 100° C., and in some embodiments, from about 55° C. to about 85° C. Likewise, the degree of crystallinity of the polymer may be from about 1% to about 35%, in some embodiments from about 3% to about 20%, and in some embodiments, from about 5% and about 25%. Through the use of a ductile propylene polymer having a relatively low melting temperature and degree of crystallinity, the window of temperatures at which the second polyolefin composition begins to melt can be broadened, which thereby improves the ability of the compositions to become adequately bonded together during formation of the composite. This melting temperature window of the second polyolefin composition can be characterized using differential scanning calorimetry as the width ($\Delta W_{f1/2}$) at the half height of the endothermic melting peak. As a result of the present invention, for instance, $\Delta W_{f1/2}$ may be about 5° C. or more, in some embodiments about 8° C. or more, and in some embodiments, from about 10° C. to about 20° C. The melting temperature of the second polyolefin composition may likewise range from about 100° C. to about 180° C., in some embodiments from about 120° C. to about 170° C., and in some embodiments, from about 150° C. to about 160° C., The width at the half height of the endothermic peak ($\Delta W_{f1/2}$), melting temperature (i.e., peak of the endothermic curve), and degree of crystallinity may all be determined as is well known in the art using differential scanning calorimetry ("DSC") in accordance with ASTM D-3417.

Any of a variety of propylene polymers having the characteristics noted above may generally be employed in the present invention. In one particular embodiment, for instance, the propylene polymer is a low crystalline homopolymer or copolymer (e.g., random or block) containing about 10 wt. % or less of co-monomers (e.g., α-olefins), and in some embodiments, about 2 wt. % or less. Such polymers are typically formed using a metallocene catalyst, either alone or in combination with a small amount of an α-olefin co-monomer. Some examples of suitable metalocene catalysts are described above. Other examples of suitable metallocene catalysts for low crystalline propylene polymers may be described in U.S. Patent Publication No. 2012/0208422 to Koori, et al. For instance, such metallocene catalysts may be obtained from a combination of a promoter and a transition metal compound that form a cross-linked structure via two cross-linking groups. Suitable promoters may include, for instance, dimethylanilinium tetrakis(pentafluorophenyl)borate, triethylammonium tetraphenylborate, tri(n-butyl)ammonium tetraphenylborate, trimethylammonium tetraphenylborate, tetraethylammonium tetraphenylborate, methyl(tri-n-butyl)ammonium tetraphenylborate, benzyl(tri-n-butyl)ammonium tetraphenylborate, aluminoxane (e.g., methylaluminoxane, ethylaluminoxane, isobutylaluminoxane, etc.), and so forth. Suitable transition metal compounds may likewise include (1,2'-dimethylsilylene) (2,1'-dimethylsilylene)bis(3-n-butyl-indenyl)zirconium dichloride, (1,2'-dimethylsilylene) (2,1'-dimethylsilylene)bis(3-trimethylsilylmethylindenyl)zirconium dichloride, (1,2'-dimethylsilylene)(2,1'-dimethylsilylene)bis(3-phenylindenyl)zirconium dichloride, (1,2'-dimethylsilylene)(2,1'-dimethylsilylene)bis(4,5-benzo-indenyl)zirconium dichloride, (1,2'-dimethylsilylene)(2,1'-dimethylsilylene)bis(4-isopropylindenyl)zirconium dichloride, (1,2'-dimethylsilylene)(2,1'-dimethylsilylene)bis(5,6-dimethylindenyl)zirconium dichloride, (1,2'-dimethylsilylene)(2,1'-dimethylsilylene)bis(4,7-di-isopropylindenyl)zirconium dichloride, (1,2'-dimethylsilylene)(2,1'-dimethylsilylene)bis(4-phenylindenyl)zirconium dichloride, (1,2'-dimethylsilylene) (2,1'-dimethylsilylene)bis(3-methyl-4-isopropylindenyl) zirconium dichloride, (1,2'-dimethylsilylene)(2,1'-dimethylsilylene)bis(5,6-benzoindenyl)zirconium dichloride, (1,2'-dimethylsilylene) (2,1'-isopropylidene)-bis(indenyl)zirconium dichloride, (1,2'-dimethylsilylene)(2,1'-isopropylidene)-bis(3-methylindenyl)zirconium dichloride, (1,2'-dimethylsilylene) (2,1'-isopropylidene)-bis(3-isopropylindenyl)zirconium dichloride, (1,2'-dimethylsilylene) (2,1'-isopropylidene)-bis(3-n-butylindenyl)zirconium dichloride, and (1,2'-dimethylsilylene)(2,1'-isopropylidene)-bis(3-trimethylsilylmethylin-denyl)zirconium dichloride, etc., as well as transition metal compounds produced by substituting zirconium in the aforementioned compounds with titanium or hafnium.

The resulting ductile propylene polymer typically has a density in the range of from 0.85 to 0.91 g/cm³, and in some embodiments, from about 0.85 to 0.089 g/cm³, such as determined in accordance with ASTM 1505-10. The ductile propylene polymer may also have a weight average molecular weight of from about 10,000 to about 200,000 grams per mole, in some embodiments from about 30,000 to about 100,000 grams per mole, and in some embodiments, from about 40,000 to about 80,000 grams per mole, as well as a polydispersity index (weight average molecular weight divided by number average molecular weight) of about 4 or less, and in some embodiments, about 3 or less. Commercially available examples of such metallocene-catalyzed propylene polymers may include, for instance, L-MODU™ S901, S600 or S400, which are available from Idemitsu Kosan.

Ductile propylene polymers generally constitute from about 0.1 wt. % to about 15 wt. %, in some embodiments from about 0.2 wt. % to about 12 wt. %, in some embodiments from about 0.5 wt. % to about 10 wt. %, and in some embodiments, from about 1 wt. % to 8 wt. % of the polymer content of the second polyolefin composition. Likewise, the ductile propylene polymers may constitute from about 0.1 wt. % to about 15 wt. %, in some embodiments from about 0.5 wt. % to about 10 wt. %, and in some embodiments, from about 1 wt. % to 8 wt. % of the entire second polyolefin composition.

C. Fatty Acid Derivative

A fatty acid derivative is also employed in the second polyolefin composition. As noted above, the weight ratio of ductile propylene polymers to fatty acid derivatives is selectively controlled in the present invention to help achieve the desired degree of softness and tactility without adversely impacting the overall durability and strength of the composition. More specifically, the weight ratio of ductile propylene polymers to fatty acid derivatives typically ranges from about 2 to about 60, in some embodiments from about 10 to about 50, in some embodiments from about 15 to about 40, and in some embodiments, from about 20 to about 30. While the actual amount may generally vary, fatty acid derivatives typically constitute from about 0.001 wt. % to about 5 wt. %, in some embodiments from about 0.01 wt. % to about 1 wt. %, and in some embodiments, from about 0.05 wt. % to about 0.5 wt. % of the second polyolefin composition.

Suitable fatty acid derivatives for use in the composition may include, for instance, fatty acid amides, fatty acid esters, fatty acid salts, and so forth. In one particular embodiment, for example, the fatty acid derivative may be a fatty acid amide. The fatty acid amide may be any suitable amide compound derived from the reaction between a fatty acid and ammonia or an amine-containing compound (e.g., a compound containing a primary amine group or a secondary amine group). The fatty acid may be any suitable fatty acid, such as a saturated or unsaturated $C_8$-$C_{28}$ fatty acid or a saturated or unsaturated $C_{12}$-$C_{28}$ fatty acid. In certain embodiments, the fatty acid may be erucic acid (i.e., cis-13-docosenoic acid), oleic acid (i.e., cis-9-octadecenoic acid), stearic acid (octadecanoic acid), behenic acid (i.e., docosanoic acid), arachic acid (i.e., arachidinic acid or eicosanoic acid), palmitic acid (i.e., hexadecanoic acid), and mixtures or combinations thereof. The amine-containing compound can be any suitable amine-containing compound, such as fatty amines (e.g., stearylamine or oleylamine), ethylenediamine, 2,2'-iminodiethanol, and 1,1'-iminodipropan-2-ol.

More particularly, the fatty acid amide may be a fatty acid amide having the structure of one of Formulae (I)-(V):

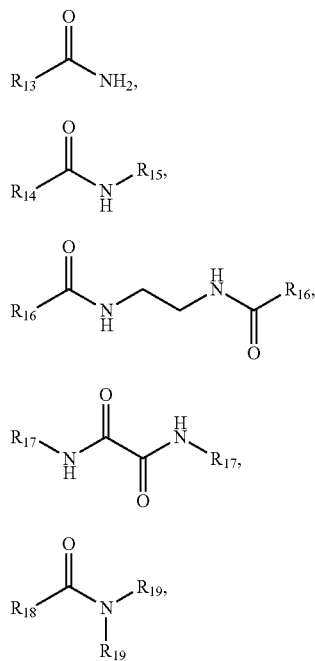

wherein, $R_{13}$, $R_{14}$, $R_{15}$, $R_{16}$, and $R_{18}$ are independently selected from $C_7$-$C_{27}$ alkyl groups and $C_7$-$C_{27}$ alkenyl groups, and in some embodiments, $C_{11}$-$C_{27}$ alkyl groups and $C_{11}$-$C_{27}$ alkenyl groups;

$R_{17}$ is selected from $C_8$-$C_{28}$ alkyl groups and $C_8$-$C_{28}$ alkenyl groups, and in some embodiments, $C_{12}$-$C_{28}$ alkyl groups and $C_{12}$-$C_{28}$ alkenyl groups; and $R_{19}$ is —$CH_2CH_2OH$ or —$CH_2CH(CH_3)OH$.

For example, the fatty acid amide may have the structure of Formula (I), where $R_{13}$ is —$CH_2(CH_2)_{10}CH$=$CH(CH_2)_7CH_3$ (erucamide), —$CH_2(CH_2)_6CH$=$CH(CH_2)_7CH_3$ (oleamide), —$CH_2(CH_2)_{15}CH_3$, —$CH_2(CH_2)_{19}CH_3$, or —$CH_2(CH_2)_{17}CH_3$. In other embodiments, the fatty acid amide may have the structure of Formula (II) where $R_{14}$ is —$CH_2(CH_2)_{10}CH$=$CH(CH_2)_7CH_3$ and $R_{15}$ is —$CH_2(CH_2)_{15}CH_3$, or where $R_{14}$ is —$CH_2(CH_2)_6CH$=$CH(CH_2)_7CH_3$ and $R_{15}$ is —$CH_2(CH_2)_{13}CH_3$. Likewise, in yet other embodiments, the fatty acid amide may have the structure of Formula (III) where $R_{16}$ is $CH_2(CH_2)_{15}CH_3$ or —$CH_2(CH_2)_6$ $CH$=$CH(CH_2)_7CH_3$. The composition may also contain a mixture of two or more such fatty acid amides.

If desired, fatty acid esters may also be employed in the present invention. Fatty acid esters may be obtained by oxidative bleaching of a crude natural wax and subsequent esterification of a fatty acid with an alcohol. The fatty acid may be a $C_8$-$C_{28}$ fatty acid or a saturated or unsaturated $C_{12}$-$C_{28}$ fatty acid, such as described above. The alcohol may have 1 to 4 hydroxyl groups and 2 to 20 carbon atoms. When the alcohol is multifunctional (e.g., 2 to 4 hydroxyl groups), a carbon atom number of 2 to 8 is particularly desired. Particularly suitable multifunctional alcohols may include dihydric alcohol (e.g., ethylene glycol, propylene glycol, butylene glycol, 1,3-propanediol, 1,4-butanediol, 1,6-hexanediol and 1,4-cyclohexanediol), trihydric alcohol (e.g., glycerol and trimethylolpropane), tetrahydric alcohols (e.g., pentaerythritol and erythritol), and so forth. Aromatic alcohols may also be suitable, such as o-, m- and p-tolylcarbinol, chlorobenzyl alcohol, bromobenzyl alcohol, 2,4-dimethylbenzyl alcohol, 3,5-dimethylbenzyl alcohol, 2,3,5-cumobenzyl alcohol, 3,4,5-trimethylbenzyl alcohol, p-cuminyl alcohol, 1,2-phthalyl alcohol, 1,3-bis(hydroxymethyl)benzene, 1,4-bis(hydroxymethyl)benzene, pseudocumenyl glycol, mesitylene glycol and mesitylene glycerol. Fatty acid salts may also be employed, such as those formed by saponification of a fatty acid to neutralize excess carboxyltic acids and form a metal salt. Saponification may occur with a metal hydroxide, such as an alkali metal hydroxide (e.g., sodium hydroxide) or alkaline earth metal hydroxide (e.g., calcium hydroxide). The resulting fatty acid salt typically includes an alkali metal (e.g., sodium, potassium, lithium, etc.) or alkaline earth metal (e.g., calcium, magnesium, etc.).

D. Optional Additives

If desired, various other additives may also be employed in the second polyolefin composition as is well known in the art. Examples of such additives may include, for instance, elastomers (e.g., styrenic elastomers, olefinic elastomers, etc.), fillers, pigments, antioxidants, stabilizers (e.g., melt stabilizers, light stabilizers, heat stabilizers, etc.), surfactants, flow promoters, solid solvents, plasticizers, particulates, bonding agents, tackifiers, viscosity modifiers, etc. When employed, such additives typically constitute from about 0.001 wt. % to about 15 wt. %, in some embodiments from about 0.01 to about 19 wt. %, and in some embodiments, from about 0.1 wt. % to about 8 wt. % of the second polyolefin composition.

In certain embodiments, for instance, the second polyolefin composition may contain an olefinic elastomer, such as a copolymer of propylene and an α-olefin. Suitable α-olefins may be linear or branched (e.g., one or more $C_1$-$C_3$ alkyl branches, or an aryl group) and formed from olefins, such as $C_2$-$C_{20}$ α-olefins, $C_2$-$C_{12}$ α-olefins, or $C_2$-$C_8$ α-olefins. Specific examples include ethylene, butene; 3-methyl-1-butene; 3,3-dimethyl-1-butene; pentene; pentene with one or more methyl, ethyl or propyl substituents; hexene with one or more methyl, ethyl or propyl substituents; heptene with one or more methyl, ethyl or propyl substituents; octene with one or more methyl, ethyl or propyl substituents; nonene with one or more methyl, ethyl or propyl substituents; ethyl, methyl or dimethyl-substituted decene; dodecene; styrene; and so forth. Particularly desired α-olefin comonomers are ethylene, butene (e.g., 1-butene), hexene, and octene (e.g., 1-octene or 2-octene). The propylene content of the propylene/α-olefin copolymer is typically from about 60 mole % to about 99.5 mole %, in some embodiments from about 80 mole % to about 99 mole %, and in some embodiments, from about 85 mole % to about 98 mole %. The α-olefin content may likewise range from about 0.5 mole % to about 40 mole %, in some embodiments from about 1 mole % to about 20 mole %, and in some embodiments, from about 2 mole % to about 15 mole %. Generally speaking, the copolymer has a density lower than that of certain polyolefins (e.g., LLDPE), but approaching and/or overlapping that of other elastomers. For example, the density of the copolymer may be about 0.91 grams per cubic centimeter (g/cm$^3$) or less, in some embodiments from about 0.85 to about 0.89 g/cm$^3$, and in some embodiments, from about 0.85 g/cm³ to about 0.88 g/cm³. Such propylene copolymers are commercially available under the designations VISTAMAXX™ from ExxonMobil Chemical Co. and VERSIFY™ available from Dow Chemical Co.

III. Nonwoven Webs

The fibers of the first and second nonwoven webs may generally have any of a variety of different configuration as is known in the art. For example, monocomponent and/or multicomponent fibers may be employed. Monocomponent fibers, for instance, are typically formed by extruding a polymer composition from a single extruder. Multicomponent fibers, on the other hand, are generally formed from two or more polymer compositions (e.g., bicomponent fibers) extruded from separate extruders. The polymer compositions may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniquchi et al. and U.S. Pat. No. 5,336,552 to Strac et al., U.S. Pat. No. 5,108,820 to Kaneko, et al., U.S. Pat. No. 4,795,668 to Krueae, et al., U.S. Pat. No. 5,382,400 to Pike, et al., U.S. Pat. No. 5,336,552 to Strack, et al., and U.S. Pat. No. 6,200,669 to Marmon, et al. Multicomponent fibers having various irregular shapes may also be formed, such as described in U.S. Pat. No. 5,277,976 to Hoqle et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al.

The fibers may constitute the entire fibrous component of the first and/or second nonwoven web or blended with other types of fibers. When blended with other types of fibers, it is normally desired that the fibers of the present invention constitute from about 20 wt % to about 95 wt. %, in some embodiments from about 30 wt. % to about 90 wt. %, and in some embodiments, from about 40 wt. % to about 80 wt. % of a web.

Any of a variety of known techniques may be employed to form the first and/or second nonwoven web. For example, in one embodiment, the first and/or second nonwoven webs may be formed by a spunbond process in which the polyolefin composition is fed to an extruder and extruded through a conduit to a spinneret. Spinnerets for extruding fibers are well known to those of skill in the art. For example, the spinneret may include a housing containing a spin pack having a plurality of plates stacked one on top of each other and having a pattern of openings arranged to create flow paths for the polymer composition. The spinneret may also have openings arranged in one or more rows that form a downwardly extruding curtain of fibers when the polymer composition is extruded therethrough. The process may also employ a quench blower positioned adjacent the curtain of fibers extending from the spinneret. Air from the quench air blower may quench the fibers as they are formed. A fiber draw unit or aspirator may also be positioned below the spinneret to receive the quenched fibers. Fiber draw units or aspirators for use in melt spinning polymers are well-known in the art. The fiber draw unit may include an elongate vertical passage through which the fibers are drawn by aspirating air entering from the sides of the passage and flowing downwardly through the passage. A heater or blower may supply aspirating air to the fiber draw unit, which draws the fibers and ambient air through the fiber draw unit.

Generally speaking, the resulting fibers of the first and/or second nonwoven web may have an average size (e.g., diameter) of about 100 micrometer or less, in some embodiments from about 0.1 microns to about 50 microns, and in some embodiments, from about 0.5 microns to about 40 microns. The fibers may likewise have a denier of about 6 or less, in some embodiments about 3 or less, and in some embodiments, from about 0.5 to about 1.5. In certain embodiments, the fibers may be in the form of substantially continuous filaments (e.g., spunbond filaments), which may have a length much greater than their diameter, such as a length to diameter ratio ("aspect ratio") of about 15,000 to 1 or more, and in some embodiments, about 50,000 to 1 or more.

The fibers may be formed into a coherent web structure by randomly depositing the fibers onto a forming surface (optionally with the aid of a vacuum) and then bonding the resulting web using any known technique, such as with an adhesive or autogenously (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with polymer composition used to form the fibers. Suitable autogenous bonding techniques may include ultrasonic bonding, thermal bonding, through-air bonding, and so forth. Typically, the resulting basis weight of each web is about 30 grams per square meter or less, in some embodiments from about 1 to about 20 grams per square meter, and in some embodiments, from about 2 to about 10 grams per square meter.

If desired, the first and/or second nonwoven web may also be subjected to one or more post-treatment steps before being combined into the composite of the present invention as is known in the art. For example, the first and/or second nonwoven web may be stretched or necked in the machine and/or cross-machine directions. Suitable stretching techniques may include necking, tentering, groove roll stretching, etc. Examples of suitable stretching techniques are described in U.S. Pat. Nos. 5,336,545, 5,226,992, 4,981,747 and 4,965,122 to Morman, as well as U.S. Patent Application Publication No. 2004/0121687 to Morman, et al. Alternatively, the nonwoven web may remain relatively inextensible in at least one direction prior to forming the composite. The nonwoven web may also be subjected to other known processing steps, such as aperturing, heat treatments, etc.

IV. Composite

Once formed, the first and second nonwoven webs may then be laminated together to form a composite using any conventional technique, such as with an adhesive or autogenously. In one embodiment, for example, the nonwoven webs may be thermally bonded by passing the webs through a nip formed between a pair of rolls, one or both of which are heated to melt-fuse the fibers. One or both of the rolls may also contain intermittently raised bond points to provide an intermittent bonding pattern. The pattern of the raised points is generally selected so that the nonwoven laminate has a total bond area of less than about 50% (as determined by conventional optical microscopic methods), and in some embodiments, less than about 30%. Likewise, the bond density is also typically greater than about 100 bonds per square inch, and in some embodiments, from about 250 to about 500 pin bonds per square inch. Such a combination of total bond area and bond density may be achieved by bonding the web with a pin bond pattern having more than about 100 pin bonds per square inch that provides a total bond surface area less than about 30% when fully contacting a smooth anvil roll. In some embodiments, the bond pattern may have a pin bond density from about 250 to about 350 pin bonds per square inch and a total bond surface area from about 10% to about 25% when contacting a smooth anvil roll. Exemplary bond patterns include, for instance, those described in U.S. Pat. No. 3,855,046 to Hansen et al., U.S. Pat. No. 5,620,779 to Levy et al. U.S. Pat. No. 5,962,112 to Havnes et al., U.S. Pat. No. 6,093,665 to Savovitz et al., U.S. Design Pat. No. 428,267 to Romano et al. and U.S. Design Pat. No. 390,708 to Brown.

Due to the particular thermal properties of the polyolefin compositions used to form the first and second nonwoven webs, the present inventors have discovered that relatively low temperatures can be used to bond the webs together. For example, the bonding temperature (e.g., the temperature of the rollers) may be relatively low, such as from about 50° C. to about 165° C., in some embodiments from about 80° C. to about 160° C., and in some embodiments, from about 100° C. to about 155° C. Likewise, the nip pressure may range from about 5 to about 150 pounds per square inch, in some embodiments, from about 10 to about 100 pounds per square inch, and in some embodiments, from about 30 to about 60 pounds per square inch.

Other types of bonding techniques may also be employed in the present invention to attach the first and second nonwoven webs. In one embodiment, for example, hydraulic entangling may be employed using conventional hydraulic entangling equipment, such as described in U.S. Pat. No. 3,485,706 to Evans. Hydraulic entangling may be carried out with any appropriate working fluid, such as, for example, water. The working fluid may flow through a manifold that evenly distributes the fluid to a series of individual holes or orifices. These holes or orifices may be from about 0.003 to about 0.015 inch in diameter and may be arranged in one or more rows with any number of orifices, e.g., 30-100 per inch, in each row. However, it should also be understood that many other manifold configurations and combinations may be used. Although not held to any particular theory of operation, it is believed that the columnar jets of working fluid that directly impact the fibers of one of the webs and drive those fibers into and partially through the other web, causing the fibers to entangle and bond together. To achieve the desired entanglement, it is typically desired that hydroentangling be performed using water pressures from about 1000 to 3000 psig, and in some embodiments, from about 1200 to 1800 psig.

The resulting composite may be a two-layered material containing only the first and second nonwoven webs. In such embodiments, the first nonwoven web typically constitutes from about 20 wt. % to about 80 wt. %, in some embodiments from about 30 wt. % to about 70 wt. %, and in some embodiments, from about 40 wt. % to about 60 wt. % of the composite, and the second nonwoven web likewise constitutes from about 20 wt. % to about 80 wt. %, in some embodiments from about 30 wt. % to about 70 wt. %, and in some embodiments, from about 40 wt. % to about 60 wt. % of the composite. The nonwoven composite typically has a basis weight of from about 1 to about 45 grams per square meter or less, in some embodiments from about 2 to about 30 grams per square meter, and in some embodiments, from about 3 to about 20 grams per square meter.

Of course, it should also be understood that the nonwoven composite may contain additional layers (e.g., nonwoven webs, films, strands, etc.) if so desired. For example, the composite may contain three (3) or more layers, and in some embodiments, from three (3) to ten (10) layers (e.g., 3 or layers). In one embodiment, for instance, the nonwoven composite may contain an inner nonwoven layer (e.g., meltblown or spunbond) positioned between two outer nonwoven layers (e.g., spunbond). For example, the inner nonwoven layer may be formed from the first polyolefin composition and one or both of the outer nonwoven layers may be formed from the second polyolefin composition. In another embodiment, the nonwoven composite may contain five (5) nonwoven layers, which includes a central nonwoven layer, two intermediate nonwoven layers overlying the central layer, and two outer nonwoven layers overlying the intermediate layers. The central layer may, for instance, be formed from the second polyolefin composition and one or both of the intermediate layers may be formed from the first polyolefin composition. If desired, the outer layers may likewise be formed from the second polyolefin composition.

Various techniques for forming laminates of this nature are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al. Of course, the laminate may have other configurations and possess any desired number of layers, such as a spunbond/meltblown/meltblown/spunbond ("SMMS") laminate, spunbond/meltblown ("SM") laminate, etc. In such embodiments, the nonwoven composite of the present invention may desirably form on or more of the spunbond layers. In yet another embodiment, the nonwoven composite may be employed in a multi-layered laminate structure in which one or more additional film layers are employed. Any known technique may be used to form a film, including blowing, casting, flat die extruding, etc. The film may be a mono- or multi-layered film. Any of a variety of polymers may generally be used to form the film layer, such as polyolefins (e.g., polyethylene, polypropylene, polybutylene, etc.); polytetrafluoroethylene; polyesters (e.g., polyethylene terephthalate, polylactic acid, etc.); polyamides (e.g., nylon); polyvinyl chloride; polyvinylidene chloride; polystyrene; and so forth. In one embodiment, for instance, the film may be formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers.

Various additional potential processing and/or finishing steps known in the art, such as slitting, stretching, etc., may be performed without departing from the spirit and scope of the invention. For instance, the composite may optionally be mechanically stretched in the cross-machine and/or machine directions to enhance extensibility. For example, the composite may be coursed through two or more rolls that have grooves in the CD and/or MD directions that incrementally stretch the composite in the CD and/or MD direction. Such grooved satellite/anvil roll arrangements are described in U.S. Patent Application Publication Nos. 2004/0110442 to Rhim, et al. and 2006/0151914 to Gerndt, et al. The grooved rolls may be constructed of steel or other hard material (such as a hard rubber). Besides grooved rolls, other techniques may also be used to mechanically stretch the composite in one or more directions. For example, the composite may be passed through a tenter frame that stretches the composite. Such tenter frames are well known in the art and described, for instance, in U.S. Patent Application Publication No. 2004/0121687 to Morman, et al. The composite may also be necked, such as described above.

Regardless of the particular manner in which it is formed, the present inventors have discovered that the resulting composite may possess a high degree of abrasion, as well as enhanced strength and toughness. For example, the composite may exhibit a relatively high "peak load", which indicates the maximum load to break as expressed in units of grams-force per inch. The MD peak load of the composite may, for instance, be about 2,000 grams-force ("$g_f$") or more, in some embodiments about 3,000 $g_f$ or more, and in some embodiments, from about 4,000 to about 15,000 gr. The CD peak load may likewise be about 1,200 $g_f$ or more, in some embodiments about 1,500 $g_f$ or more, and in some embodiments, from about 2,000 to about 10,000 $g_f$. In addition, the nonwoven composite is also capable of exhibiting improved "peak elongation" properties, i.e., the percent elongation of the composite at its peak load. For example, the nonwoven composite of the present invention may exhibit a machine direction ("MD") peak elongation of about 20% or more, in some embodiments about 30% or more, and in some embodiments, from about 40% to about 70%. The nonwoven composite may also exhibit a cross-machine direction ("CD") peak elongation of about 35% or more, in some embodiments about 45% or more, and in some embodiments, from about 50% to about 80%.

Of course, in addition to possessing good mechanical properties, the nonwoven composite of the present invention is also soft, drapable, and tactile. One parameter that is indicative of the softness of the composite is the peak load ("cup crush load") as determined according to the "cup crust" test, which is described in more detail below. More particularly, the cup crush load of the composite may, for instance, be about 200 $g_f$ or less, in some embodiments about 150 $g_f$ or less and in some embodiments, from about 5 to about 100 $g_f$. Another parameter that is indicative of the good tactile properties of the composite is the static coefficient of friction in the machine or cross-machine direction. More particularly, the MD and/or CD coefficient of friction may be about 0.885 or less, in some embodiments about 0.850 or less, and in some embodiments, from about 0.500 to about 0.800.

If desired, the nonwoven composite of the present invention may be applied with various treatments to impart desirable characteristics. For example, the composite may be treated with liquid-repellency additives, antistatic agents, surfactants, colorants, antifogging agents, fluorochemical blood or alcohol repellents, lubricants, and/or antimicrobial agents. In addition, the composite may be subjected to an electret treatment that imparts an electrostatic charge to improve filtration efficiency. The charge may include layers of positive or negative charges trapped at or near the surface of the polymer, or charge clouds stored in the bulk of the polymer. The charge may also include polarization charges that are frozen in alignment of the dipoles of the molecules. Techniques for subjecting a fabric to an electret treatment are well known by those skilled in the art. Examples of such techniques include, but are not limited to, thermal, liquid-contact, electron beam and corona discharge techniques. In one particular embodiment, the electret treatment is a corona discharge technique, which involves subjecting the laminate to a pair of electrical fields that have opposite polarities. Other methods for forming an electret material are described in U.S. Pat. No. 4,215,682 to Kubik, et al.; U.S. Pat. No. 4,375,718 to Wadsworth; U.S. Pat. No. 4,592,815 to Nakao; U.S. Pat. No. 4,874,659 to Ando; U.S. Pat. No. 5,401,446 to Tsai, et al.; U.S. Pat. No. 5,883,026 to Reader, et al; U.S. Pat. No. 5,908,598 to Rousseau, et al.; U.S. Pat. No. 6,365,088 to Knight, et al.

V. Articles

The nonwoven composite of the present invention may be used in a wide variety of applications. For example, the nonwoven laminate may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches, and so forth. Materials and processes suitable for forming such absorbent articles are well known to those skilled in the art. Typically, absorbent articles include a substantially liquid-impermeable layer (e.g., backsheet), a liquid-permeable layer (e.g., topsheet, surge layer, etc.), and an absorbent core.

In certain embodiments, for example, the nonwoven composite of the present invention may be used to form the topsheet and/or backsheet of the absorbent article. When used to form the backsheet, the nonwoven composite may also be laminated to a film, such as described above. The film is typically liquid-impermeable and either vapor-permeable or vapor-impermeable. Films that are liquid-impermeable and vapor-permeable are often referred to as "breathable" and they typically have a water vapor transmission rate ("WVTR") of about 100 grams per square meter per 24 hours ($g/m^2/24$ hours) or more, in some embodiments from about 500 to about 20,000 $g/m^2/24$ hours, and in some embodiments, from about 1,000 to about 15,000 $g/m^2/24$ hours. The breathable film may also be a microporous or monolithic film. Microporous films are typically formed by incorporating a filler (e.g., calcium carbonate) into the polymer matrix, and thereafter stretching the film to create the pores. Examples of such films are described, for instance, in U.S. Pat. No. 5,843,057 to McCormack; U.S. Pat. No. 5,855,999 to McCormack; U.S. Pat. No. 5,932,497 to Morman, et al.; U.S. Pat. No. 5,997,981 to McCormack, et al.; U.S. Pat. No. 6,002,064 to Kobylivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No. 6,461,457 to Taylor, et al.

Regardless of how it is employed, one particularly beneficial aspect of the present invention is that the second nonwoven web, which is formed from a propylene-based composition that includes a rigid propylene polymer, ductile propylene polymer, and fatty acid derivative, can be positioned so that it defines an outwardly facing surface of the absorbent article. More particularly, the unique properties of the propylene-based composition can allow it to impart a soft and cloth-like feel to an outwardly facing surface, which was conventionally only partially achievable with polyethylene materials (e.g., LLDPE breathable film) and generally not possible with polypropylene materials. Furthermore, contrary to polyethylene materials, the propylene-based second nonwoven web can exhibit an improved degree of abrasion resistance and mechanical strength, making it even better served to define the outwardly facing surface of an absorbent article. When used in a backsheet, for example, the second nonwoven web may define a "garment-facing surface", which generally refers to an outwardly facing surface of an absorbent article that is intended to be disposed away from the body of a wearer during ordinary use. The surface is typically placed adjacent to the wearer's undergarments when the article is worn. Likewise, when used in a topsheet, the second nonwoven web may define a "body-facing surface", which generally refers to an outwardly facing surface of an absorbent article that is intended to be disposed toward or placed adjacent to the body of a wearer during ordinary use.

Various embodiments of an absorbent article that may be formed according to the present invention will now be described in more detail. Referring to FIG. 1, for instance, one embodiment of an absorbent article 201 is shown in the form of a diaper. However, as noted above, the invention may be embodied in other types of absorbent articles, such as incontinence articles, sanitary napkins, diaper pants, feminine napkins, children's training pants, and so forth. In the illustrated embodiment, the absorbent article 201 is shown as having an hourglass shape in an unfastened configuration. However, other shapes may of course be utilized, such as a generally rectangular shape, T-shape, or I-shape. As shown, the absorbent article 201 includes a chassis 202 formed by various components, including a backsheet 217, topsheet 205, absorbent core 203, and surge. It should be understood, however, that other layers may also be used in the present invention. Likewise, one or more of the layers referred to in FIG. 1 may also be eliminated in certain embodiments of the present invention.

As indicated above, the backsheet 217 may be formed from the nonwoven composite of the present invention. In fact, as discussed, the nonwoven composite may be positioned so that the second nonwoven web defines a garment-facing surface 333 of the absorbent article 201. The absorbent article 201 also includes a topsheet 205. The topsheet 205 is generally employed to help isolate the wearer's skin from liquids held in the absorbent core 203. For example, the topsheet 205 may define a body-facing surface 218, which is typically compliant, soft feeling, and non-irritating to the wearer's skin. If desired, the topsheet 205 may be formed from the nonwoven composite of the present invention. In fact, as discussed, the nonwoven composite may be positioned so that the second nonwoven web defines the body-facing surface 218 if so desired. Alternatively, the topsheet may include a conventional a nonwoven web (e.g., spun-bond web, meltblown web, or bonded carded web). Other exemplary topsheet constructions that contain a nonwoven web are described in U.S. Pat. Nos. 5,192,606; 5,702,377; 5,931,823; 6,060,638; and 6,150,002, as well as U.S. Patent Application Publication Nos. 200410102750, 200510054255, and 2005/0059941.

As illustrated in FIG. 1, the absorbent article 201 may also include a surge layer 207 that helps to decelerate and diffuse surges or gushes of liquid that may be rapidly introduced into the absorbent core 203. Desirably, the surge layer 207 rapidly accepts and temporarily holds the liquid prior to releasing it into the storage or retention portions of the absorbent core 203. In the illustrated embodiment, for example, the surge layer 207 is interposed between an inwardly facing surface 216 of the topsheet 205 and the absorbent core 203. Alternatively, the surge layer 207 may be located on the outwardly facing surface 218 of the topsheet 205. The surge layer 207 is typically constructed from highly liquid-permeable materials. Suitable materials may include porous woven materials, porous nonwoven materials, and apertured films. In one embodiment, the surge layer 207 may also be formed from the nonwoven composite of the present invention. Other examples of suitable surge layers are described in U.S. Pat. No. 5,486,166 to Ellis, et al. and U.S. Pat. No. 5,490,846 to Ellis, et al.

Besides the above-mentioned components, the absorbent article 201 may also contain various other components as is known in the art. For example, the absorbent article 201 may also contain a substantially hydrophilic wrapsheet (not illustrated) that helps maintain the integrity of the fibrous structure of the absorbent core 203. The wrapsheet is typically placed about the absorbent core 203 over at least the two major facing surfaces thereof, and composed of an absorbent cellulosic material, such as creped wadding or a high wet-strength tissue. The wrapsheet may be configured to provide a wicking layer that helps to rapidly distribute liquid over the mass of absorbent fibers of the absorbent core 203. The wrapsheet material on one side of the absorbent fibrous mass may be bonded to the wrapsheet located on the opposite side of the fibrous mass to effectively entrap the absorbent core 203. Furthermore, the absorbent article 201 may also include a ventilation layer (not shown) that is positioned between the absorbent core 203 and the backsheet 217. When utilized, the ventilation layer may help insulate the backsheet 217 from the absorbent core 203, thereby reducing dampness in the backsheet 217. Examples of such ventilation layers may include a nonwoven web laminated to a breathable film, such as described in U.S. Pat. No. 6,663,611 to Blaney, et al. If desired, such nonwoven webs may be formed from the composite of the present invention.

In some embodiments, the absorbent article 201 may also include a pair of ears (not shown) that extend from the side edges 232 of the absorbent article 201 into one of the waist regions. The ears may be integrally formed with a selected diaper component. For example, the ears may be integrally formed with the backsheet 217 or from the material employed to provide the top surface. In alternative configurations, the ears may be provided by members connected and assembled to the backsheet 217, the top surface, between the backsheet 217 and top surface, or in various other configurations.

As representatively illustrated in FIG. 1, the absorbent article 201 may also include a pair of containment flaps 212 that are configured to provide a barrier and to contain the lateral flow of body exudates. The containment flaps 212 may be located along the laterally opposed side edges 232 of the topsheet 205 adjacent the side edges of the absorbent core 203. The containment flaps 212 may extend longitudinally along the entire length of the absorbent core 203, or may only extend partially along the length of the absorbent core 203. When the containment flaps 212 are shorter in length than the absorbent core 203, they may be selectively positioned anywhere along the side edges 232 of absorbent article 201 in a crotch region 210. In one embodiment, the containment flaps 212 extend along the entire length of the absorbent core 203 to better contain the body exudates. Such containment flaps 212 are generally well known to those skilled in the art. For example, suitable constructions and arrangements for the containment flaps 212 are described in U.S. Pat. No. 4,704,116 to Enloe.

The absorbent article 201 may include various elastic or stretchable materials, such as a pair of leg elastic members 206 affixed to the side edges 232 to further prevent leakage of body exudates and to support the absorbent core 203. In addition, a pair of waist elastic members 208 may be affixed to longitudinally opposed waist edges 215 of the absorbent article 201. The leg elastic members 206 and the waist elastic members 208 are generally adapted to closely fit about the legs and waist of the wearer in use to maintain a positive, contacting relationship with the wearer and to effectively reduce or eliminate the leakage of body exudates from the absorbent article 201. The absorbent article 201 may also include one or more fasteners 230. For example, two flexible fasteners 130 are illustrated in FIG. 1 on opposite side edges of waist regions to create a waist opening and a pair of leg openings about the wearer. The shape of the fasteners 230 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 230 includes a separate piece of hook material affixed to the inside surface of a flexible backing.

The various regions and/or components of the absorbent article 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the backsheet 217 and topsheet 205 are assembled to each other and to the absorbent core 203 using an adhesive. Alternatively, the absorbent core 203 may be connected to the backsheet 217 using conventional fasteners, such as buttons, hook and loop type fasteners, adhesive tape fasteners, and so forth. Similarly, other diaper components, such as the leg elastic members 206, waist elastic members 208 and fasteners 230, may also be assembled into the absorbent article 201 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth.

The present invention may be better understood with reference to the following examples.

Test Methods

Thermal Properties:

The melting temperature and degree of crystallinity of a material may be determined by differential scanning calorimetry ("DSC") in accordance with ASTM D-3417. The differential scanning calorimeter was a DSC Q 2000 (T-zero cell0, which may be outfitted with a liquid nitrogen cooling accessory and with a UNIVERSAL ANALYSIS 2000 (version 4.6.6) analysis software program, both of which are available from T.A. Instruments Inc. To avoid directly handling the samples, tweezers or other tools may be used. The sample (e.g., 4 milligrams) may be placed into an aluminum pan and weighed to an accuracy of 0.01 milligram on an analytical balance. A lid may be crimped over the material sample onto the pan. Typically, the sample is placed directly in the weighing pan. The differential scanning calorimeter may be calibrated using an indium metal standard and a baseline correction was performed, as described in the operating manual for the differential scanning calorimeter. A sample may be placed into the test chamber of the differential scanning calorimeter for testing, and an empty pan may be used as a reference. All testing may be run with a 55-cubic centimeter per minute nitrogen (industrial grade) purge on the test chamber. The heating and cooling program may be a 2-cycle test that begins with an equilibration of the chamber to −50° C., followed by a first heating period at a heating rate of 10° C. per minute to a temperature of 225° C., equilibration of the sample at 225° C. for 3 minutes, and a first cooling period at a cooling rate of 10° C. per minute to a temperature of −50° C., a second heating period at a heating rate of 10° C. per minute to a temperature of 225° C., equilibration of the sample at 225° C. for 3 minutes, and then a second cooling period at a cooling rate of 10° C. per minute to a temperature of −50° C. All testing may be conducted in an inert gas atmosphere (e.g., helium).

The results may be evaluated using the UNIVERSAL ANALYSIS 2000 analysis software program, which identifies and quantifies the endothermic and exothermic peaks, and the areas under the peaks on the DSC plots. The melting temperature is determined using an automatic inflection calculation. The areas under the peaks on the DSC plots are determined in terms of joules per gram of sample (J/g). For example, the heat of fusion of a sample (Alt) is determined by integrating the area of the endothermic peak. The area values are determined by converting the areas under the DSC plots (e.g. the area of the endotherm) into the units of joules per gram (J/g) using computer software. The exothermic heat of crystallization ($\Delta H_c$) can be determined during the first cooling cycle. If desired, the % crystallinity may also be calculated as follows:

$$\% \text{ crystallinity} = 100^*(A-B)/C$$

wherein,

A is the sum of endothermic peak areas during the heating cycle (J/g);

B is the sum of exothermic peak areas during the heating cycle (J/g); and

C is the heat of fusion for the selected polymer where such polymer has 100% crystallinity (J/g). The areas under any exothermic peaks encountered in the DSC scan due to insufficient crystallinity may also be subtracted from the area under the endothermic peak to appropriately represent the degree of crystallinity.

Tensile Properties:

The strip tensile strength values were determined in substantial accordance with ASTM Standard D-5034. Specifically, a sample was cut or otherwise provided with size dimensions that measured 3 inches (76.2 millimeters) (width)×6 inches (152.4 millimeters) (length). A constant-rate-of-extension type of tensile tester was employed. The tensile testing system was a Sintech Tensile Tester, which is available from MTS Corp. of Eden Prairie, Minn. The tensile tester was equipped with TESTWORKS 4.08B software from MTS Corporation to support the testing. An appropriate load cell was selected so that the tested value fell within the range of 10-90% of the full scale load. The sample was held between grips having a front and back face measuring 1 inch (25.4 millimeters)×3 inches (76 millimeters). The grip faces were rubberized, and the longer dimension of the grip was perpendicular to the direction of pull. The grip pressure was pneumatically maintained at a pressure of 60 to 80 pounds per square inch. The tensile test was run at a 20 inches per minute rate with a gauge length of 4 inches and a break sensitivity of 40%. Three samples were tested along the machine-direction ("MD") and three samples were tested by along the cross direction ("CD"). In addition, the ultimate tensile strength ("peak load"), and peak elongation was also recorded.

Martindale Abrasion:

This test can measure the relative resistance of a sample to abrasion according to Worldwide Strategic Partners ("WSP") Standard Test No. 20.5 (08). A circular specimen of 165 mm±6.4 mm in diameter with an area of 18,258 sq mm is subjected to a requested number of cycles (10 or 60) with an abradant under a pressure of 9 kilopascals (kPa). The abradant is a 36 inch by 4 inch by 0.05 thick silicone rubber wheel reinforced with fiberglass having a rubber surface hardness 81A Durometer, Shore A of 81±9. The specimen is examined for the presence of surface fuzzing (fiber lofting), pilling (small dumps of fibers), roping, delamination or holes and assigned a numerical rating of 1, 2, 3, 4, or 5 based on comparison to a set of standard photographs similarly numbered, with "1" showing the greatest wear and "5" the least. The test is carried out with a Martindale Wear and Abrasion Tester such as Model No. 103 or 403 from James H. Heal & Company, Ltd. of West Yorkshire, England.

Cup Crush Softness:

The softness of a sample may also be measured according to the "cup crush" test according to WSP Standard Test No. 402.0 (09), which evaluates softness by measuring the peak load ("cup crush load") that is required for a hemi-spherically shaped foot (4.5 cm diameter) to crush a sample (23 cm×23 cm) into an inverted cup shape (approximately 6.5 cm diameter×6.5 cm tall) while the cup-shaped sample remains surrounded by a cylinder (approximately 6.5 cm diameter) to maintain uniform deformation. An average of 10 readings is used. The foot and cup are aligned to avoid contact between the cup walls and the foot which could affect the readings. The peak load is measured while the foot is descending at a rate of about 380 mm per minute and is measured in grams. The cup crush test also yields a value for the total energy required to crush a sample (the cup crush energy), which is the energy from the start of the test to the peak load point, i.e. the area under the curve formed by the load in grams on the one axis and the distance the foot travels in millimeters on the other. Cup crush energy is therefore reported in g*mm. Lower cup crush values indicate a softer material. One suitable device for measuring cup crush is a model FTD-G-500 load cell (500 gram range) available from the Schaevitz Company of Pennsauken, N.J.

Static and Dynamic Coefficient of Friction:

Coefficient of Friction testing may be performed in accordance with ASTM D 1894-08 using a high gloss smooth vinyl tile sliding surface. A sled, which has the test specimen attached thereto, may be pulled over a high gloss smooth vinyl tile surface. The test specimen and the vinyl tile surface are in surface-to-surface contact with each other. The coefficient of friction value is defined as the measure of the relative difficulty when the surface of the test specimen slid over the fixed vinyl tile surface. The "static" coefficient of friction is the highest instantaneous value obtained to begin movement between the surfaces and "dynamic" coefficient of friction is the average of the values obtained during the 60 seconds of the test (6 inch travel distance). The testing apparatus may be a LAB MASTER Slip and Friction Model 32-90 with a model number 32.90-06 test sled; both of which are available from Testing Machines, Inc. of Islanda, N.Y., 11722, U.S.A.

The sled used for the testing may have a weight of 200 grams. Testing occurs in a room having a temperature of between about 22° C. and about 24° C., and a relative humidity of about 50%. The test material is mounted to the platen (table) had a length of about 305 millimeters and a width of about 102 to 127 millimeters using a double-sided tape. The test specimen has a length of about 100 millimeters and a width of about 63 millimeters. The sled is lowered by the test equipment before testing and positioned lightly onto the test material when the test was started to prevent any unnatural bond from developing. The length of the sled and the length the plane-mounted are parallel. The moving platen is then put in motion at a velocity of 6 inches per minute. The gauge takes readings and continues to do so for about 60 seconds (6 inches of travel). The gauge measures and stored the "static" value for the highest instantaneous coefficient of friction value obtained to begin the movement between the surfaces within the first inch of pull. The "dynamic" value is obtained and stored as the average of the values obtained during the 60 seconds of the test (6 inch travel distance).

The coefficient of friction evaluation was performed five times for each sample.

Example 1

A first polyolefin composition was formed that contained 100 wt. % of a LLDPE polymer and a second polyolefin composition was formed that contained 97.4 wt. % of a rigid propylene homopolymer, 2.5 wt. % of a ductile propylene homopolymer, and 0.1 wt. % of erucamide. The rigid propylene polymer was PP 3155 (Exxonmobl), which has a density of 0.9 g/cm$^3$, melting temperature of about 165° C., and a tensile modulus of about 1300 to 2000 MPa. The ductile propylene polymer was L-MODU™ S901 (Idemitsu), which has a density of 0.87 g/cm$^3$, melting temperature of 70° C., and a tensile modulus of 80 MPa. The first polyolefin composition was spun to form a first nonwoven web using the following conditions: pump speed of 55 rpm, throughput of 194 kg/hr, melt temperature of 213° C., cabin pressure of 3000 bar, and process air temperature of 25° C. The second polyolefin composition was spun to form a second nonwoven web using the following conditions: pump speed of 55 rpm, throughput of 199 kg/hr, melt temperature of 233° C., cabin pressure of 4400 bar, and process air temperature of 20° C. The first and second nonwoven webs were then thermally bonded together between a calendar roll heated to 132° C. and an embossing roll heated to 114° C., wherein the nip pressure was 100 N/mm. The bond pattern covered 18.5% of the area of the surface of the composite. The resulting composite had a total basis weight of 14 gsm (each nonwoven web having a basis weight of about 7 gsm), and the fibers of both webs had an average size of about 1.5 µm.

Example 2

A nonwoven composite was formed as described in Example 1, except that the first polyolefin composition was spun to form a first nonwoven web using the following conditions: pump speed of 55 rpm, throughput of 195 kg/hr, melt temperature of 214° C., cabin pressure of 3000 bar, and process air temperature of 25° C. The second polyolefin composition was also spun to form a second nonwoven web using the following conditions: pump speed of 55 rpm, throughput of 199 kg/hr, melt temperature of 232° C., cabin pressure of 4400 bar, and process air temperature of 20° C. The resulting composite had a total basis weight of 16 gsm (each nonwoven web having a basis weight of about 8 gsm), and the fibers of both webs had an average size of about 1.5 µm.

Example 3

A nonwoven composite was formed as described in Example 1, except that the first polyolefin composition was spun to form a first nonwoven web using the following conditions: pump speed of 55 rpm, throughput of 195 kg/hr, melt temperature of 214° C., cabin pressure of 3000 bar, and process air temperature of 25° C. The second polyolefin composition was also spun to form a second nonwoven web using the following conditions: pump speed of 55 rpm, throughput of 199 kg/hr, melt temperature of 239° C., cabin pressure of 4400 bar, and process air temperature of 20° C. The first and second nonwoven webs were then thermally bonded together between a calendar roll heated to 130'C and an embossing roll heated to 114° C., wherein the nip pressure was 100 N/mm. The bond pattern covered 18.5% of the area of the surface of the composite. The resulting composite had a total basis weight of 14 gsm (each nonwoven web having a basis weight of about 7 gsm), and the fibers of both webs had an average size of about 1.5 µm.

Example 4

A nonwoven composite was formed as described in Example 1, except that the first polyolefin composition was spun to form a first nonwoven web using the following conditions: pump speed of 50 rpm, throughput of 194 kg/hr, melt temperature of 213° C., cabin pressure of 3000 bar, and process air temperature of 25° C. The second polyolefin composition was also spun to form a second nonwoven web using the following conditions: pump speed of 50 rpm, throughput of 199 kg/hr, melt temperature of 241° C., cabin pressure of 4400 bar, and process air temperature of 20° C. The first and second nonwoven webs were then thermally bonded together between a calendar roll heated to 130° C. and an embossing roll heated to 111° C., wherein the nip pressure was 100 N/mm. The bond pattern covered 18.5% of the area of the surface of the composite. The resulting composite had a total basis weight of 16 gsm (each nonwoven web having a basis weight of about 8 gsm), and the fibers of both webs had an average size of about 1.5 µm.

Example 5

A polyolefin composition was formed that contained 100 wt. % of PP 3155 (Exxonmobil). The composition was spun to form a nonwoven web using the following conditions: pump speed of 55 rpm, throughput of 199 kg/hr, melt temperature of 233° C., cabin pressure of 4400 bar, and process air temperature of 20° C. The resulting nonwoven web had a total basis weight of 18 gsm and the fibers had an average size of about 1.5 µm.

Example 6

A polyolefin composition was formed that contained 95 wt. % of PP 3155 (Exxonmobil) and 5 wt. % L-MODU™ S901 (Idemitsu). The composition was spun to form a nonwoven web using the following conditions: pump speed of 61 rpm, throughput of 221 kg/hr, melt temperature of 228° C., cabin pressure of 4400 bar, and process air temperature of 20° C. The resulting nonwoven web had a total basis weight of 15 gsm and the fibers had an average size of about 1.5 µm.

Example 7

A polyolefin composition was formed that contained 94.8 wt. % of PP 3155 (Exxonmobil), 5 wt. % L-MODU™ S901 (Idemitsu), and 0.2 wt. % erucamide. The composition was spun to form a nonwoven web using the following conditions: pump speed of 55 rpm, throughput of 199 kg/hr, melt temperature of 233° C., cabin pressure of 4400 bar, and process air temperature of 20° C. The resulting nonwoven web had a total basis weight of 15 gsm and the fibers had an average size of about 1.5 µm.

Example 8

A polyolefin composition was formed that contained 94.8 wt. % of PP 3155 (Exxonmobil), 5 wt. % L-MODU™ S901 (Idemitsu), and 0.2 wt. % erucamide. The composition was spun to form a nonwoven web using the following conditions: pump speed of 61 rpm, throughput of 221 kg/hr, melt temperature of 228° C., cabin pressure of 4400 bar, and process air temperature of 20° C. The resulting nonwoven web had a total basis weight of 18 gsm and the fibers had an average size of about 1.5 µm.

The abrasion resistance (Martindale), softness (Cup Crush, Coefficient of Friction), and tensile properties (Peak Load and Elongation) of the samples formed according to Examples 1-8 were then tested as described above. The results are set forth in Tables 1-4 below.

TABLE 1

| | Martindale Abrasion Resistance | | | |
|---|---|---|---|---|
| | Abrasion 10 cycles @ 9 kPa | | Abrasion 60 cycles @ 9 kPa | |
| Example | Rating No. | Std. Deviation | Rating No. | Std. Deviation |
| 1 | 3 | 1 | 1 | 0 |
| 2 | 4 | 0 | 1 | 0 |
| 3 | 4 | 0 | 1 | 0 |
| 4 | 4 | 1 | 1 | 0 |
| 5 | 5 | 1 | 1 | 1 |
| 6 | 5 | 1 | 1 | 1 |
| 7 | 5 | 0 | 2 | 1 |
| 8 | 5 | 0 | 3 | 1 |

TABLE 2

| | Cup Crush Softness | | | |
|---|---|---|---|---|
| | Cup Crush | | | |
| | Peak Load (gf) | | Total energy (gf * mm) | |
| Example | Avg. | Std. Dev. | Avg. | Std. Dev. |
| 1 | 32.78 | 4.91 | 631.86 | 47.05 |
| 2 | 39.13 | 4.78 | 740.51 | 57.26 |
| 3 | 35.68 | 5.59 | 691.40 | 66.48 |
| 4 | 46.75 | 3.45 | 955.65 | 58.80 |
| 5 | 140.37 | 19.74 | 2978.15 | 190.34 |
| 6 | 120.92 | 8.09 | 2530.06 | 46.76 |
| 7 | 68.49 | 6.34 | 1335.93 | 121.87 |
| 8 | 102.66 | 20.42 | 2358.88 | 351.29 |

TABLE 3

| | Coefficient of Friction | | | | | | | |
|---|---|---|---|---|---|---|---|---|
| | MD | | | | CD | | | |
| | Static | | Dynamic | | Static | | Dynamic | |
| Example | Avg. | Std. Dev. | Avg. | Std. Dev. | Avg. | Std. Dev. | Avg. | Std. Dev. |
| 1 | 0.886 | 0.023 | 0.860 | 0.035 | 0.780 | 0.032 | 0.761 | 0.032 |
| 2 | 0.763 | 0.021 | 0.731 | 0.038 | 0.754 | 0.078 | 0.705 | 0.042 |
| 3 | 0.932 | 0.102 | 0.878 | 0.080 | 0.763 | 0.066 | 0.765 | 0.049 |
| 4 | 0.880 | 0.054 | 0.845 | 0.058 | 0.748 | 0.044 | 0.731 | 0.039 |
| 5 | 0.514 | 0.021 | 0.422 | 0.017 | 0.482 | 0.022 | 0.438 | 0.021 |
| 6 | 0.584 | 0.043 | 0.519 | 0.029 | 0.532 | 0.042 | 0.468 | 0.022 |
| 7 | 0.599 | 0.039 | 0.520 | 0.044 | 0.551 | 0.031 | 0.505 | 0.025 |
| 8 | 0.670 | 0.069 | 0.558 | 0.059 | 0.564 | 0.025 | 0.504 | 0.034 |

TABLE 4

| | Tensile Properties | | | | | | | |
|---|---|---|---|---|---|---|---|---|
| | MD | | | | CD | | | |
| | Peak Load (gf) | | Peak Elongation (%) | | Peak Load (gf) | | Peak Elongation (%) | |
| Ex. | Avg. | Std. Dev. | Avg. | Std. Dev. | Avg. | Std. Dev. | Avg. | Std. Dev. |
| 1 | 2034.52 | 166.99 | 22.6 | 2.6 | 766.62 | 59.94 | 37.5 | 3.0 |
| 2 | 2162.19 | 43.92 | 23.0 | 1.7 | 726.43 | 92.60 | 35.1 | 5.8 |
| 3 | 2153.20 | 76.85 | 23.7 | 2.5 | 846.85 | 117.56 | 40.0 | 4.2 |
| 4 | 2349.81 | 87.96 | 22.0 | 1.9 | 904.07 | 79.54 | 38.5 | 3.5 |
| 5 | 3610.35 | 558.49 | 25.8 | 3.6 | 1603.00 | 207.33 | 40.2 | 6.6 |
| 6 | 4284.49 | 157.77 | 34.7 | 4.0 | 1587.11 | 107.75 | 47.6 | 4.0 |
| 7 | 4284.42 | 427.21 | 36.6 | 3.3 | 1524.36 | 39.35 | 44.7 | 5.1 |
| 8 | 5349.72 | 369.89 | 35.3 | 2.8 | 1963.74 | 190.26 | 45.8 | 3.0 |

Example 9

A first polyolefin composition was formed that contained 100 wt. % of a LLDPE polymer and a second polyolefin composition was formed that contained 93 wt. % PP 3155 (Exxonmobil), 5 wt. % L-MODU™ S901 (Idemitsu), and 2 wt. % of a mixture of erucamide and titanium dioxide. The first polyolefin composition was spun to form a first nonwoven web using the following conditions: pump speed of 52 rpm, throughput of 202 kg/hr, melt temperature of 210° C., cabin pressure of 0.028 bar, and process air temperature of 25° C. The second polyolefin composition was spun to form a second nonwoven web using the following conditions: pump speed of 49 rpm, throughput of 195 kg/hr, melt temperature of 250° C., cabin pressure of 0.05 bar, and process air temperature of 20° C. The first and second nonwoven webs were then thermally bonded together between a calendar roll heated to 128° C. (PE-side) and an embossing roll heated to 132° C. (PP-side), wherein the nip pressure was 100 N/mm. The bond pattern covered 18% of the area of the surface of the composite. The resulting composite had a total basis weight of 17.2 gsm (each nonwoven web having a basis weight of about 8.6 gsm), and the fibers of both webs had an average size of about 1.7 μm.

Example 10

A nonwoven composite was formed as described in Example 9, except that a third nonwoven web was employed so that the second nonwoven web was positioned between the first and third nonwoven webs. The third nonwoven web was formed from the same polyolefin composition as the first nonwoven web. The webs were then thermally bonded together between a calendar roll heated to 135° C. and an embossing roll heated to 140° C., wherein the nip pressure was 100 N/mm. The bond pattern covered 18% of the area of the surface of the composite. The resulting composite had a total basis weight of 17.6 gsm (each nonwoven web having a basis weight of about 8.8 gsm), and the fibers of both webs had an average size of about 1.6 μm.

The abrasion resistance (Martindale), softness (Cup Crush, Coefficient of Friction), and tensile properties (Peak Load and Elongation) of the samples formed according to Examples 9-10 were then tested as described above. The results are set forth in Tables 5-8 below.

TABLE 5

| | Martindale Abrasion Resistance | | | |
|---|---|---|---|---|
| | Abrasion 10 cycles @ 9 kPa | | Abrasion 60 cycles @ 9 kPa | |
| Example | Rating No. | Std. Deviation | Rating No. | Std. Deviation |
| 9 | 4 | 0 | 1 | 0 |
| 10 | 4 | 0 | 1 | 0 |

TABLE 6

| | Cup Crush Softness | | | |
|---|---|---|---|---|
| | Cup Crush | | | |
| | Peak Load (gf) | | Total energy (gf * mm) | |
| Example | Avg. | Std. Dev. | Avg. | Std. Dev. |
| 9 | 105.07 | 7.87 | 1921.73 | 151.13 |
| 10 | 105.01 | 10.11 | 1996.35 | 81.04 |

TABLE 7

| | Coefficient of Friction | | | | | | | |
|---|---|---|---|---|---|---|---|---|
| | MD | | | | CD | | | |
| | Static | | Dynamic | | Static | | Dynamic | |
| Example | Avg. | Std. Dev. | Avg. | Std. Dev. | Avg. | Std. Dev. | Avg. | Std. Dev. |
| 9 | 0.609 | 0.015 | 0.579 | 0.010 | 0.615 | 0.025 | 0.605 | 0.019 |
| 10 | 0.730 | 0.036 | 0.773 | 0.024 | 0.710 | 0.038 | 0.747 | 0.035 |

TABLE 8

| | Tensile Properties | | | | | | | |
|---|---|---|---|---|---|---|---|---|
| | MD | | | | CD | | | |
| | Peak Load (gf) | | Peak Elongation (%) | | Peak Load (gf) | | Peak Elongation (%) | |
| Example | Avg. | Std. Dev. | Avg. | Std. Dev. | Avg. | Std. Dev. | Avg. | Std. Dev. |
| 9 | 2681.28 | 102.95 | 23.1 | 1.7 | 1181.63 | 78.54 | 37.9 | 7.5 |
| 10 | 3374.30 | 368.88 | 24.0 | 2.7 | 1499.21 | 189.10 | 35.8 | 3.1 |

Example 11

A polyolefin composition was formed that contained 88 wt. % of PP 3155 (Exxonmobil), 5 wt. % of L-MODU™ S400 (Idemitsu), 5 w. % of Exxon Vistamaxx™ 7050 and 2 wt. % of erucamide. L-MODU™ S400 (Idemitsu) has a density of 0.87 g/cm³, melting temperature of 70° C., tensile modulus of 80 MPa, and a melt flow rate of 2,000 g/10 min (230° C., 2.16 kg). The polyolefin composition was spun to form a nonwoven web using the following conditions: pump speed of 13.7 rpm, throughput of 100 kg/hr, melt temperature of 225° C., (FDU) Fiber Drawing Unit pressure of 0.50 bar, and process air temperature of 20° C. The resulting nonwoven web had a total basis weight of 15 gsm.

Example 12

A nonwoven web was formed as described in Example 11, except that the polyolefin composition was 88 wt. % of PP 3155 (Exxonmobil), 5 wt. % of L-MODU™ S400 (Idemitsu), 5 w. % of Vistamaxx™ 2330 and 2 wt. % of erucamide.

Example 13

A nonwoven web was formed as described in Example 11, except that the polyolefin composition was 88 wt. % of PP 3155 (Exxonmobil), 10 wt. % of L-MODU™ S400 (Idemitsu), and 2 wt. % of erucamide.

Example 14

A nonwoven web was formed as described in Example 11, except that the polyolefin composition was 93 wt. % of PP 3155 (Exxonmobil), 5 wt. % of L-MODU™ S400 (Idemitsu), and 2 wt. % of erucamide.

The abrasion resistance (Martindale), softness (Cup Crush), and tensile properties (Peak Load and Elongation) of the samples formed according to Examples 11-14 were then tested as described above. The results are set forth in Tables 9-11 below.

TABLE 9

| Martindale Abrasion Resistance | | |
|---|---|---|
| | Abrasion 10 cycles @ 9 kPa | |
| Example | Rating No. | Std. Deviation |
| 11 | 5 | 1 |
| 12 | 5 | 1 |
| 13 | 5 | 0 |
| 14 | 5 | 0 |

TABLE 10

| Cup Crush Softness | | | | |
|---|---|---|---|---|
| | Cup Crush | | | |
| | Peak Load (gf) | | Total energy (gf * mm) | |
| Example | Avg. | Std. Dev. | Avg. | Std. Dev. |
| 11 | 56.45 | 3.10 | 1019.22 | 89.98 |
| 12 | 58.64 | 4.14 | 1085.34 | 64.48 |
| 13 | 73.44 | 9.84 | 1384.63 | 158.82 |
| 14 | 107.64 | 7.51 | 2001.86 | 118.44 |

TABLE 11

| | Tensile Properties | | | | | | | |
|---|---|---|---|---|---|---|---|---|
| | MD | | | | CD | | | |
| | Peak Load (gf) | | Peak Elongation (%) | | Peak Load (gf) | | Peak Elongation (%) | |
| Example | Avg. | Std. Dev. | Avg. | Std. Dev. | Avg. | Std. Dev. | Avg. | Std. Dev. |
| 11 | 3808.90 | 357.22 | 37.7 | 3.8 | 1324.76 | 84.62 | 46.0 | 7.9 |
| 12 | 3249.10 | 149.59 | 31.0 | 1.7 | 1527.03 | 197.30 | 44.1 | 4.9 |
| 13 | 3401.39 | 107.44 | 32.7 | 1.1 | 1526.31 | 162.23 | 47.4 | 5.0 |
| 14 | 4175.17 | 276.63 | 43.7 | 4.0 | 2043.65 | 136.09 | 51.6 | 1.6 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A nonwoven composite comprising:
a first nonwoven web containing a plurality of fibers formed from a first polyolefin composition, wherein the first polyolefin composition contains at least one ethylene polymer, wherein the ethylene polymer constitutes at least 80 wt. % of the polymer content of the first polyolefin composition and has a modulus of elasticity of from 50 to 500 MPa as determined in accordance with ASTM D638-10; and
a second nonwoven web positioned adjacent to the first nonwoven web, the second nonwoven web containing a plurality of fibers formed from a second polyolefin composition, wherein the second polyolefin composition contains at least one rigid propylene polymer, 0.1 wt. % to about 15 wt. % of at least one ductile propylene homopolymer, and at least one fatty acid derivative, wherein the at least one ductile propylene polymer and the at least one fatty acid derivative are contained in the second polyolefin composition at a ratio of the at least one ductile propylene polymer to the at least one fatty acid derivative of about 10 to about 50; and
wherein the nonwoven composite exhibits a machine direction peak load of 2,000 grams-force or more and/or a cross-machine direction peak load of 1,200 grams-force or more, as determined in accordance with ASTM Standard D-5034; and
wherein the nonwoven composite exhibits a machine direction peak elongation of 20% or more and/or a cross-machine direction peak elongation of 35% or more, as determined in accordance with ASTM Standard D-5034.

2. The nonwoven composite of claim 1, wherein the first polyolefin composition has a melting temperature of from 50° C. to 145° C.

3. The nonwoven composite of claim 1, wherein the ethylene polymer is linear low density polyethylene.

4. The nonwoven composite of claim 1, wherein the rigid propylene polymer has a modulus of elasticity of from 800 to 4,000 MPa, as determined in accordance with ASTM D638-10.

5. The nonwoven composite of claim 1, wherein the rigid propylene polymer is an isotactic homopolymer of propylene.

6. The nonwoven composite of claim 1, wherein rigid propylene polymer constitutes from 80 wt. % to 99.5 wt. % of the second polyolefin composition.

7. The nonwoven composite of claim 1, wherein the ratio of the modulus of elasticity of the rigid propylene polymer to the modulus of elasticity of the ductile propylene polymer is from 1 to 50, as determined in accordance with ASTM D638-10.

8. The nonwoven composite of claim 7, wherein the modulus of elasticity of the ductile polymer is from 1 to 500 MPa, as determined in accordance with ASTM D638-10.

9. The nonwoven composite of claim 1, wherein the ductile polymer has a melting temperature of from 40° C. to 120° C.

10. The nonwoven composite of claim 1, wherein the ductile polymer has a degree of crystallinity of from 1% to 35%, as determined using differential scanning calorimetry in accordance with ASTM D-3417.

11. The nonwoven composite of claim 1, wherein the ductile polymer is a metallocene-catalyzed homopolymer of propylene.

12. The nonwoven composite of claim 1, wherein the width at the half height of the endothermic peak of the second polyolefin composition is 5° C. or more, as determined using differential scanning calorimetry in accordance with ASTM D-3417.

13. The nonwoven composite of claim 1, wherein the ductile propylene polymer constitutes from 0.2 wt. % to 12 wt. % of the second polyolefin composition and/or the fatty acid derivative constitutes from 0.01 wt. % to 5 wt. % of the second polyolefin composition.

14. The nonwoven composite of claim 1, wherein the weight ratio of the ductile polymer to the fatty acid derivative in the second polyolefin composition is from 15 to 40.

15. The nonwoven composite of claim 1, wherein the fatty acid derivative is a fatty acid amide.

16. The nonwoven composite of claim 1, wherein the second polyolefin composition further comprises a propylene/α-olefin copolymer.

17. The nonwoven composite of claim 1, wherein the first nonwoven web, the second nonwoven web, or both are a spunbond web.

18. The nonwoven composite of claim 1, wherein the first nonwoven web constitutes from 20 wt. % to 80 wt. % of the composite and the second nonwoven web constitutes from 20 wt. % to 80 wt. % of the composite.

19. The nonwoven composite of claim 1, wherein the composite exhibits a cup crush load of 200 grams-force or less and/or a coefficient of friction in the machine direction of 0.885 or less.

20. A multi-layered laminate comprising the nonwoven composite of claim 1 and an additional layer, which is a nonwoven web, film, or a combination thereof.

21. An absorbent article comprising an absorbent core positioned between a backsheet and a topsheet, wherein the backsheet, topsheet, or both contains the nonwoven composite of claim 1.

22. The nonwoven composite of claim 1, wherein the nonwoven composite exhibits a machine direction peak elongation of 30% or more and/or a cross-machine direction peak elongation of 45% or more, as determined in accordance with ASTM Standard D-5034.

23. The nonwoven composite of claim 1, wherein the fatty acid derivative constitutes from 2 wt. % to 5 wt. % of the second polyolefin composition.

24. The nonwoven composite of claim 15, wherein the fatty acid amide comprises erucamide, oleamide, or a combination thereof.

\* \* \* \* \*